(12) United States Patent
Jansen et al.

(10) Patent No.: US 12,171,201 B2
(45) Date of Patent: *Dec. 24, 2024

(54) INSECT BREEDING DEVICE

(71) Applicant: Protix B.V., Dongen (NL)

(72) Inventors: Jaco Jansen, Breda (NL); Hendrikus Ant Schol, Waspik (NL); Bastiaan Frederik Jürgens, Rotterdam (NL)

(73) Assignee: Protix B.V., Dongen (NL)

( * ) Notice: Subject to any disclaimer, the term of this patent is extended or adjusted under 35 U.S.C. 154(b) by 275 days.

This patent is subject to a terminal disclaimer.

(21) Appl. No.: 17/615,591

(22) PCT Filed: Jun. 3, 2020

(86) PCT No.: PCT/NL2020/050357
§ 371 (c)(1),
(2) Date: Dec. 1, 2021

(87) PCT Pub. No.: WO2020/246880
PCT Pub. Date: Dec. 10, 2020

(65) Prior Publication Data
US 2022/0304288 A1 Sep. 29, 2022

Related U.S. Application Data

(60) Provisional application No. 62/858,339, filed on Jun. 7, 2019.

(30) Foreign Application Priority Data

Jun. 14, 2019 (NL) ..................................... 2023313

(51) Int. Cl.
*A01K 67/033* (2006.01)
*F26B 3/04* (2006.01)

(52) U.S. Cl.
CPC .............. *A01K 67/033* (2013.01); *F26B 3/04* (2013.01)

(58) Field of Classification Search
CPC ........ A01K 67/033; A01K 1/01; A01K 31/18; F26B 3/04
(Continued)

(56) References Cited

U.S. PATENT DOCUMENTS

| | | | | |
|---|---|---|---|---|
| 3,750,625 A | * | 8/1973 | Edwards | A01K 67/033 119/6.6 |
| 4,324,200 A | * | 4/1982 | Johnson | A01K 67/033 119/200 |
| 4,418,647 A | * | 12/1983 | Hoffman | A01K 67/033 119/6.6 |

(Continued)

FOREIGN PATENT DOCUMENTS

| | | |
|---|---|---|
| BE | 893734 A | 11/1982 |
| CN | 206284043 U | 6/2017 |

(Continued)

*Primary Examiner* — Tye William Abell
*Assistant Examiner* — Maria E Graber
(74) *Attorney, Agent, or Firm* — N.V. Nederlandsch Octrooibureau

(57) ABSTRACT

An insect breeding device comprising includes at least one insect cage having a top wall with a non-curved and flat surface or having a top wall with a concave inner surface; a bin for holding a cleaning liquid; and a first pipe for receiving the cleaning liquid and entering the cage through a first opening; a nozzle (14), coupled to the first pipe, positioned inside the at least one insect cage configured to deliver the cleaning liquid to the interior of the at least one insect cage; and a second pipe (4), coupled to a second opening (12), and located in the bottom wall of the cage and/or located in a side wall of the cage, in the side wall portion where the bottom wall and said side wall intersect configured to drain the cleaning liquid and the debris remaining from farming insects in the cage.

19 Claims, 9 Drawing Sheets

(58) Field of Classification Search
USPC .......................................... 119/6.6, 6.5, 243
See application file for complete search history.

(56) References Cited

U.S. PATENT DOCUMENTS

| | | | | |
|---|---|---|---|---|
| 5,178,094 | A * | 1/1993 | Carr | A01K 67/033 119/6.5 |
| 5,771,841 | A * | 6/1998 | Boor | A01K 1/031 119/452 |
| 6,041,741 | A * | 3/2000 | Gabriel | B01D 53/9409 119/419 |
| 6,244,213 | B1 * | 6/2001 | Tedders | A01K 67/033 119/6.6 |
| 6,474,259 | B1 * | 11/2002 | Gaugler | A01K 67/033 119/6.7 |
| 6,588,373 | B1 * | 7/2003 | Strzempko | A01K 1/031 119/416 |
| 8,733,284 | B2 * | 5/2014 | Courtright | A01K 67/033 119/6.6 |
| 11,406,091 | B2 * | 8/2022 | Jansen | A01K 1/01 |
| 2003/0150394 | A1 * | 8/2003 | Wolfe | A01K 63/042 119/246 |
| 2011/0296756 | A1 * | 12/2011 | Zhang | A01K 39/00 119/6.5 |
| 2017/0311612 | A1 * | 11/2017 | Leo | A21D 2/34 |

FOREIGN PATENT DOCUMENTS

| | | | |
|---|---|---|---|
| CN | 109006702 A | 12/2018 | |
| FR | 3046333 A1 | 7/2017 | |
| WO | WO-02087321 A2 * | 11/2002 | ........... A01K 67/033 |
| WO | 2019125165 A1 | 6/2019 | |

* cited by examiner

INSECT BREEDING DEVICE

TECHNOLOGICAL FIELD

The invention relates to an insect breeding device used for insect breeding such as large-scale industrial insect breeding wherein for example the insects are black soldier fly. The invention also relates to a device for cleaning of an insect breeding cage.

BACKGROUND

Rearing and breeding insects at an industrial and economically feasible scale is gaining momentum for its potential as an alternative source of animal lipids, fat, proteins, amino-acids, fatty acids, etc., compared to those currently provided by, for example, the livestock industry. However, bringing the current state of the art of insect farming, especially the breeding of insects, from a small scale to such an industrial scale poses challenges not encountered in research currently done in the laboratory. Known methods for farming insects are, for example, labor-intensive with at best a handful of aspects being automated.

One of the major drawbacks of scaling up a known insect breeding device is that there are no suitable methods or means for efficaciously cleaning insect cages.

SUMMARY

It is an object of the invention to provide a solution to at least some of the aforementioned drawbacks of small-scale insect farming, especially the breeding of insects, in view of scaling up to a scale that is economically feasible.

In a first aspect of the invention this object is achieved by an insect breeding device comprising at least one insect cage, a bin for holding a cleaning liquid, a first pipe connected to the bin for receiving the cleaning liquid, wherein the pipe is entering the at least one insect cage through a first opening in the at least one insect cage, a nozzle, coupled to the first pipe, positioned inside the at least one insect cage configured to deliver the cleaning liquid to the interior of the at least one insect cage, and a second pipe, coupled to a second opening in the at least one insect cage, different from the first opening, in the at least one insect cage, configured to drain the cleaning liquid and debris remaining from farming insects in the insect cage from the at least one insect cage.

A preferred embodiment is the insect breeding device of the invention comprising at least one insect cage, wherein the top wall of said cage has a concave surface, seen from the interior side of the insect cage.

An embodiment is the insect breeding device according to the invention, wherein the second opening of the at least one insect cage is located in a side wall of the insect cage, in a portion of said side wall where the bottom floor and the side wall provided with the second opening intersect, such that the second opening is located at the lowest point of the insect cage relative to the horizontal when the side wall of the insect cage is directed vertically.

An embodiment is the insect breeding device according to the invention, wherein the second opening of the at least one insect cage is located in the bottom floor of the insect cage, such that the second opening is located at the lowest point of the insect cage relative to the horizontal when the side walls of the insect cage are directed vertically.

An embodiment is the insect breeding device according to the invention, further comprising a gas drying apparatus provided with a ventilator for generating a gas flow; a third pipe coupled to a third opening of the insect cage for transporting the gas flow inside the at least one insect cage, and a fourth opening of the insect cage for releasing the gas out of the at least one insect cage.

An embodiment is the insect breeding device according to the invention, further comprising a heater 160 for heating the generated gas flow.

In a second aspect of the invention this object is achieved by an insect breeding device comprising at least one insect cage, the insect cage having a bottom floor, side walls and a top wall, wherein the top wall has a concave surface, seen from the interior side of the insect cage; a bin for holding a cleaning liquid; a first pipe connected to the bin for receiving the cleaning liquid, wherein the pipe is entering the at least one insect cage through a first opening in the at least one insect cage; a nozzle, coupled to the first pipe, positioned inside the at least one insect cage configured to deliver the cleaning liquid to the interior of the at least one insect cage; and a second pipe, coupled to a second opening in the at least one insect cage, different from the first opening in the at least one insect cage, configured to drain the cleaning liquid and debris remaining from farming insects in the insect cage from the at least one insect cage. Optionally, the second opening is located in a side wall of the insect cage.

This arrangement enables efficient cleaning of the one or more insect cages, since the cleaning liquid enters the insect cage(s) upon being sprayed to the interior via the nozzle, the cleaning liquid removes the debris from the interior and is drained via the second opening.

It is preferred that the insect breeding device further comprises a gas drying apparatus provided with a ventilator for generating a gas flow; a third pipe coupled to a third opening of the insect cage for transporting the gas flow inside the at least one insect cage, and a fourth opening of the insect cage for transporting the gas out of the at least one insect cage. Optionally, the insect breeding device further comprises a heater for heating the generated gas flow, such that heated gas can be transported and flow inside the at least one insect cage.

An embodiment is the insect breeding device, wherein the second opening of the at least one insect cage is located in the bottom floor of the insect cage, or alternatively is located in a side wall of the insect cage, in a portion of said side wall where the bottom floor and the side wall provided with the second opening intersect, such that the second opening is located at the lowest point of the insect cage relative to the horizontal when the side walls of the insect cage are directed vertically. Thus, the second opening is in an embodiment located in a side wall of the insect cage in a portion of said side wall that intersects with the bottom floor of the insect cage, at the edge formed by the side wall and the bottom floor. Optionally, the second opening is located in a corner of the insect cage, either in the bottom floor, or in a side wall.

An embodiment is the insect breeding device, wherein the at least one insect cage further comprises a tapered bottom floor surface at the interior of the insect cage, the tapering directed such that the second opening is located at the lowest point of the insect cage relative to the horizontal when the side walls of the insect cage are directed vertically.

Having clean cages for breeding insects is a prerequisite for successful egg harvesting, and therefore there is a need to clean the insect cage at the start of the insect breeding cycle when re-using the cages from a previous insect breeding cycle. Without discarding, for example, the remains of the pupae after adult insects emerged from these, i.e. the pupal exoskeleton or exuvia, and without discarding the dead insects, feces, uncollected eggs and insects that are still alive, from the cage before loading the cage with fresh pupae reduces the chance of an efficient egg harvest, and may even hamper the ability to harvest any insect eggs at all. That is to say, gravid female insects, such as black soldier flies, are tempted to lay eggs (referred to as "ovipositioning") in the vicinity of or in any suitable food source for the eggs to hatch. The olfactory attractant emerging from exuvia and dead insects stimulate the gravid flies to oviposition in areas of the cage other than at the desired location for ovipositioning, i.e. the "ovisite". Thus, the most likely consequence of not thoroughly cleaning the cage is sub-optimal egg collection. Currently, thorough cleaning of insect cages is a time and labor intensive activity, and hampers the scaling-up of insect breeding and egg collection at an industrial scale. Of course, insufficient cleaning of the cages also introduces the risk of emerging diseases, growth of microbes such as bacteria, yeasts and mold, for adversely influencing the insect colony.

In a preferred embodiment, the insect breeding device further comprises a gas drying apparatus provided with a ventilator for generating a gas flow, optionally a heater for heating the generated gas flow, a third pipe coupled to a third opening of the insect cage for transporting the (heated) gas flow inside the at least one insect cage, and a fourth opening of the insect cage for transporting the gas out of the at least one insect cage. The (heated) gas, for example air, enables fast drying of the interior of the insect cage.

In a still further embodiment, the insect breeding device further comprises a liquid clearance device coupled to the second pipe and the bin, provided with a filter configured to separate the cleaning liquid from the debris and to deliver the cleaning liquid to the bin through a fifth pipe. This arrangement enables recycling of the cleaning liquid.

In one embodiment the filter comprises a sieve configured to separate the debris from the cleaning liquid, and a debris receptacle configured to collect the debris separated by the sieve.

In further embodiment, the cleaning liquid comprises water and at least one non-foaming detergent.

In further embodiment the cleaning liquid comprises between 0.5 percent and 10 percent of the non-foaming detergent by volume of the total cleaning liquid.

In a further embodiment the cleaning liquid comprises of a mixture of potassium, amine compounds, silicates, phosphates, non-ionogenic and amphoteric humidifiers and complexing agents.

In a further embodiment the nozzle is a fluid nozzle comprising one of a spiral liquid spray nozzle, a full-cone nozzle, a deflector plate nozzle, a solid jet nozzle, and a nozzle with a rotating head. One of the nozzles can be selected and mounted in the insect cage for efficient cleaning.

An embodiment is the insect breeding device, further comprising a first valve, coupled to the first opening, configured to open or close the first opening, and a second valve, coupled to the second opening, configured to open or close the second opening.

In a further embodiment, the insect breeding device further comprises a first pump, positioned between the first opening and the bin, configured to deliver cleaning liquid to the interior of the at least one insect cage with a predetermined flow rate and a predetermined liquid pressure.

In an embodiment the pressure of the cleaning liquid transported by the first pump is in the range between 1.5 and 6 bar.

In an embodiment the volume of cleaning liquid delivered into the at least one insect cage is in the range between 10 and 500 liters per minute. The inventors established that after breeding or rearing insects in the insect cage, such as adult black soldier flies, the insects for example farmed inside the insect cage for a period of 1 day-5 days, the amount of debris and the extent of adherence of said debris to any surface in the interior of the insect cage is such that cleaning the insect cage afterwards by applying the insect breeding device, with a volume of 10-500 liters cleaning liquid per minute for a time period of 2-180 minutes is effective and sufficient for providing a cleaned insect cage suitable for use in a subsequent round of insect breeding.

An embodiment is the insect breeding device, wherein the second opening has a cross-sectional surface area such that said second opening is arranged to drain a volume of cleaning liquid in the drainage range between 10 liters per minute and 500 liters per minute. An embodiment is the insect breeding device according to the invention, wherein the second opening is arranged to drain at least the predetermined flow rate of the cleaning liquid.

In a further embodiment, the insect breeding device further comprises a second pump, positioned between the second opening and the bin, configured to transport the cleaning liquid and debris from the at least one insect cage to the bin.

In a further embodiment, the insect breeding device further comprises a third valve coupled to the third opening configured to open or close the third opening, and a fourth valve coupled to the fourth opening configured to open or close the fourth opening.

In a further embodiment, the insect breeding device further comprises a controller connected to the first valve and the second valve and the first pump and second pump, wherein the controller is arranged to switch between a first state and a second state, wherein in the first state the first and second valves are closed and the first and second pumps are switched off, and in the second state, wherein the first valve is open and the second valve is open, the first pump is switched on and the second pump is switched on, and the controller is further arranged to control the first pump to transport the cleaning liquid at a predetermined flow rate and pressure through the nozzle, and to control the second pump to transport the cleaning liquid and debris from the second opening to the liquid clearing device.

In a further embodiment the controller is further arranged to maintain the second state for a period between 2 minutes and 180 minutes, such as between 20 and 120 minutes. Typically, a cleaning cycle performed by the insect breeding device is completed in 30-90 minutes, such as between 45 minutes and 75 minutes, typically in about 1 hour. The insect breeding device is capable of cleaning between 1 and 150 insect cages in parallel, typically 2-100 insect cages, such as 5-30 insect cages simultaneously.

In one embodiment, the insect breeding device further comprises a heater, wherein the heater is arranged to deliver the cleaning liquid to the first pump at a temperature in the range of 20° C.-85° C., such as a temperature in the range of 25° C.-65° C., for example between 31.5° C. and 32° C. A further advantage is that the heater comprised by the insect breeding device is also applicable for providing cleaning liquid to the first pump at a different temperature, such as between 15° C. and 31.5° C., such as about 25° C., and such as 32° C.-65° C., for example about 35° C. or 50° C. Cleaning liquid applied at these temperatures allows for efficient and sufficient removal of dead insect corpses, faeces, drinking water, other sources of debris, from any surface inside the insect cage and via the second opening out of the interior of the insect cage. Applying cleaning liquid at a temperature above ambient temperature also contributes to (faster) drying of the interior of the cages, at the end of a cleaning cycle by applying the insect breeding device. An embodiment is the insect breeding device according to the invention, further comprising a heater arranged between the bin and the first pump connected to the controller, wherein the heater is further arranged to deliver the cleaning liquid to the first pump at a temperature in the range of 20° C.-85° C., in particular in the range of 25° C.-65° C., more particular in the range between 31.5° C. and 32° C.

A further embodiment is the insect breeding device, wherein the at least one insect cage is arranged to have round corners in the inner surface of the cage.

An embodiment is the insect breeding device, wherein the at least one insect cage has a substantially block shape having rounded corners in the inner surface of the cage.

In a further embodiment, the at least one insect cage is manufactured using rotation molding, of a polymer blend, preferably comprising polyethylene. An advantage of a polymer blend comprising polyethylene is the beneficial capacity of the polymer to expel water droplets and cleaning liquid droplets to such an extent that these droplets do not adhere and accumulate at the concave surface of the top wall of the insect cage (seen from the interior of the insect cage), nor to the essential vertically directed side walls of the insect cage, when the insect breeding device is in operation. Herewith, cleaning liquid comprising water does not adhere at the inner surfaces of the insect cage, does not remain at the surface, though flows towards the bottom floor 17 of the insect cage and then subsequently to the second opening acting as a drain for drainage of cleaning liquid out of the interior of the insect cage. This way, the risk for droplets of cleaning liquid left at the interior surface of the insect cage is addressed such that in a new cycle of breeding insects in the insect cage, insects are not exposed to cleaning liquid, which may otherwise be hazardous to the insect and/or the insect may otherwise be drowned in the spilled cleaning liquid. A second measure to prevent droplets from accumulating inside the cage during and after a cleaning cycle by applying the insect breeding device, is the application of the gas drying apparatus, after cleaning liquid has been flushed through the insect cage. Gas, such as heated gas, flowing through the cleaned cage efficiently further dries the interior walls of the insect cage.

In a further embodiment, the at least one insect cage is further configured to have inner dimensions of a width between 30 cm and 250 cm, a depth between 50 cm and 300 cm and a height between 10 cm and 160 cm, for example a width between 30 cm and 150 cm, a depth between 50 cm and 200 cm and a height between 10 cm and 60 cm. The skilled person will appreciate that insect cages with any of the dimensions outside these ranges are also applicable for incorporation in the insect breeding device, as long as cleaning efficiency is sufficient. That is to say, an insect cage with larger dimension(s) may require a longer cleaning cycle period than 2-180 minutes, such as 240 minutes, and/or the volume of cleaning liquid is in the range of more than 500 liters per minute, such as 550-1000 liters per minute, and as a consequence, the second opening then has a cross-sectional surface area such that said second opening is arranged to drain a volume of cleaning liquid in the drainage range of over 500 liters per minute, as well. As said, the insect breeding has a second opening which is arranged to drain at least the predetermined flow rate of the cleaning liquid in certain embodiments of the invention.

An embodiment is the insect breeding device, wherein the second opening of the at least one insect cage is located in the bottom floor of the insect cage, such that the second opening is located at the lowest point of the insect cage relative to the horizontal when the side walls of the insect cage are directed vertically. An embodiment is the insect breeding device, wherein the second opening of the at least one insect cage is located in a side wall of the insect cage, in a portion of said side wall where the bottom floor and the side wall provided with the second opening intersect, such that the second opening is located at the lowest point of the insect cage relative to the horizontal when the side walls of the insect cage are directed vertically. Thus, the second opening is always the lowest point relative to the horizontal when the insect breeding device is in operation. This way, cleaning liquid, and optionally water flushed through the insect cage after the cleaning cycle, for washing away remaining film of cleaning liquid as the case may be, efficiently and adequately flows over the side walls of the insect cage, over the bottom floor and through the second opening out of the insect cage.

In a further embodiment, the at least one insect cage further comprises a tapered surface on the surface coupled to the second opening. Thus, an embodiment is the insect breeding device, wherein the at least one insect cage further comprises a tapered bottom floor surface at the interior of the insect cage, the tapering directed such that the second opening is located at the lowest point of the insect cage relative to the horizontal when the side walls of the insect cage are directed vertically. The skilled person will appreciate that the combination of a tapered bottom floor with the direction of the tapering directed towards the second opening acting as a drain, contributes to the efficient drainage of liquid such as cleaning liquid or water from the interior of the insect cage outwardly.

In a further embodiment, the second opening is configured to have a width between 2 cm and 14 cm, preferably between 3 cm and 10 cm, more preferably around 5 cm. Thus, an embodiment is the insect breeding device, wherein the second opening is configured to have a width between 2 cm and 14 cm, such as between 3.5 cm and 8 cm, for example about 5 cm. A second opening having a width of for example about 4-6 cm prevents debris that is flowing over the side walls and over the bottom floor of the insect cage towards the second opening in the bottom floor or in a side wall of the insect cage, over the for example tapered bottom floor surface, from bridging and therewith preventing the second opening from becoming clogged with debris during the cleaning of the cage by applying the insect breeding device.

As said, in an embodiment the cleaning liquid that is applied in the insect breeding device comprises a mixture of potassium, amine compounds, silicates, phosphates, non-ionogenic and amphoteric humidifiers and complexing agents, and for example the cleaning liquid consists of a mixture of potassium, amine compounds, silicates, phosphates, non-ionogenic and amphoteric humidifiers and complexing agents. The inventors established that a cleaning liquid comprising or consisting of these compounds provides for efficient and sufficient cleaning of insect cages used for farming insects, when the cleaning liquid is applied with the insect breeding device.

In a further embodiment, the nozzle is further configured to have a spray angle between 240° and 300°, preferably about 270° for a solid nozzle, or between 90° and 120° for a spiral nozzle, and a spray pattern arranged as a solid cone or solid jets from a sphere. Typically, the inventors established that by applying the cleaning liquid with the insect cleaning device by using any of such a nozzle, such a nozzle being configured to spray and flush the cleaning liquid at the indicated range of spray angle, the insect cages that require cleaning after being used for insect breeding, before a next round of insect farming starts, the insect cages are cleaned efficiently and sufficiently.

In further embodiment, the nozzle is arranged to be positioned centrally in the inner volume of the at least one insect cage.

In a different embodiment, the insect breeding device comprises a further nozzle, both nozzles positioned off-center, in the inner volume of the insect cage.

In a further embodiment, the insect breeding device comprises at least two insect cages that are stacked with each other. In this arrangement multiple insect cages can be arranged in a horizontal or vertical direction so that a space efficient arrangement can be obtained. An embodiment is the insect breeding device, comprising two insect cages stacked horizontally or vertically with each other. A further embodiment is the insect breeding device, comprising two-eight hundred insect cages stacked horizontally with each other and/or two-fifteen insect cages stacked vertically with each other, for example five-three hundred fifty horizontally stacked insect cages and/or three-seven vertically stacked insect cages, such as five-three hundred fifty horizontally stacked insect cages times three-seven vertically stacked insect cages. For example, insect cages wherein the second opening is located in a side wall of the insect cage, in a portion of said side wall where the bottom floor and the side wall provided with the second opening intersect, such that the second opening is located at the lowest point of the insect cage relative to the horizontal when the side walls of the insect cage are directed vertically, are suitable for space efficient stacking in the vertical direction. With the second opening arranged at the side of the insect cage, the second pipe points sideward, therewith preventing space under the insect cage from being occupied by this second pipe. Typically, insect cages are stacked vertically such that adjacent insect cages in the vertical direction are spaced at between 5 cm and 40 cm, such as about 10 cm or 15 cm. A further embodiment is therefore the insect breeding device according to the invention, comprising a stack of insect cages of length (l) times height (h) times breadth (b) wherein l, h and b run from 2 to 500 (l) cages, from 2 to 20 (h) cages, and from 1 to 200 (b) cages. Such high numbers of insect cages comprised by the insect breeding device of the invention makes economically feasible breeding of insects such as black soldier fly possible: the yield and production volumes of e.g. eggs is sufficiently high; cages are reusable for a large number of subsequent breeding cycles; cleaning is now made possible, without the need of labor intensive manual cleaning, though through automated cleaning cycles, to name a few advantages achieved with the operation of the insect breeding device of the invention.

DETAILED DESCRIPTION

Figure 1:
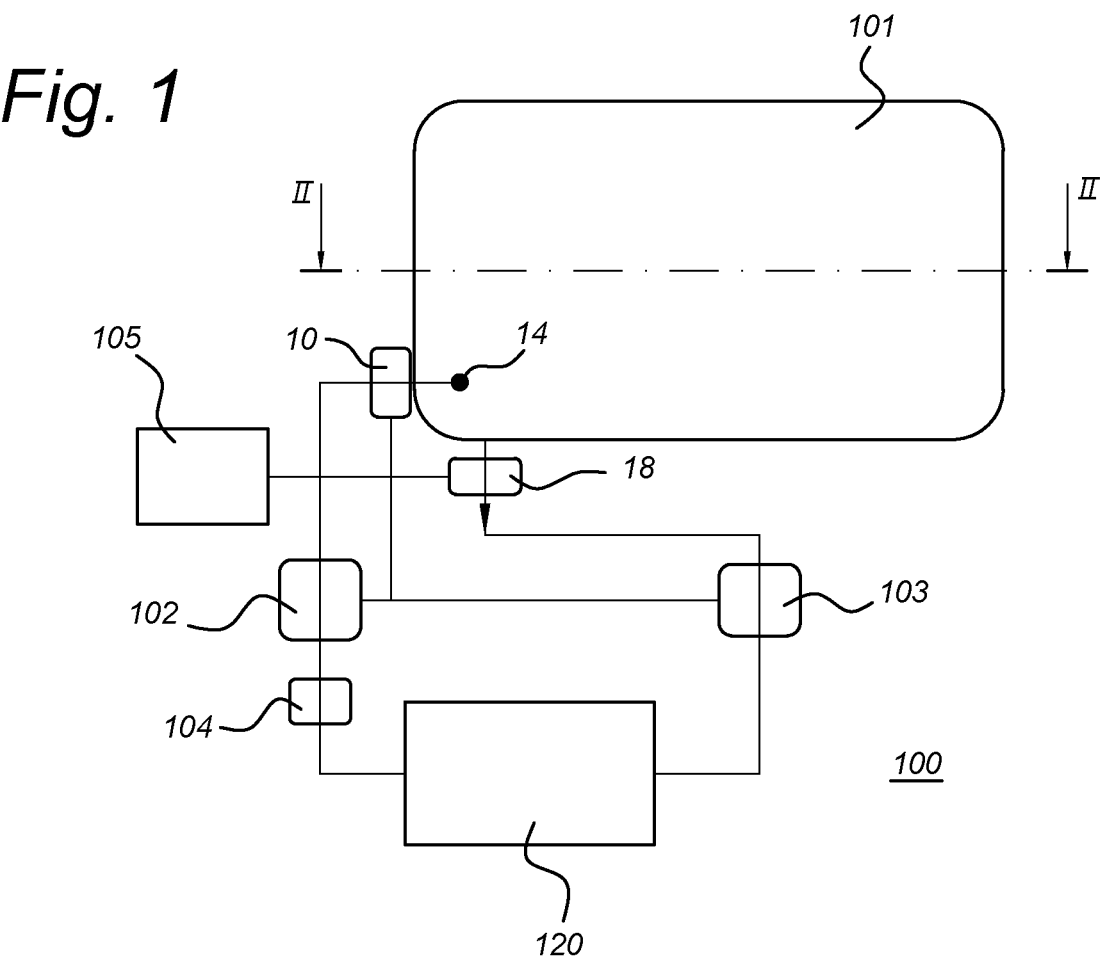
FIG. 1 (FIG. 1) illustrates a first embodiment of an insect breeding device of the present invention.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

Furthermore, the various embodiments, although referred to as "preferred" or "e.g." or "for example" or "in particular"

are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present invention, the only enumerated components of the device are A and B, and further the claim should be interpreted as including equivalents of those components.

The present invention is an insect breeding device that allows the cleaning of insect cages at a large scale. Use of the insect breeding device makes cleaning of the insect cage by hand superfluous, i.e. demands less labor. Furthermore, with the insect breeding device of the invention, cleaning multiple insect cages becomes controllable with regards to, for example, the intensity of the cleaning cycle and the timing of the procedure on a cage-by-cage basis. An important advantage of the insect breeding device of the invention is its applicability and suitability for use in cleaning insect cages impermeable for fluid and applicable for industrial scale breeding of insects. Moreover, since currently applied cages for breeding insects are inaccessible for manual cleaning after a breeding cycle, the insect breeding device of the invention solves the problem of the ability to provide cleaned cages after each breeding cycles such that contamination does not occur between subsequently farmed herds of insects, and solved the problem that cages are reusable upon the automated cleaning in between breeding cycles, which is not possible with cages not part of the insect breeding device of the invention.

FIG. 1 and FIG. 2 show the insect breeding device 100 according to a first and second embodiment of the present invention. The insect breeding device comprises an insect cage 101 with a bin 120 for holding cleaning liquid. A pipe 3 is connected from the bin 120 to the first opening 11 of the insect cage 101. A nozzle 14, coupled to the first pipe 3, is positioned inside the insect cage and is configured to deliver cleaning liquid to the interior of the insect cage. A second pipe 4 connects the second opening 12 of the insect cage 101 to the bin 120.

The cleaning liquid flows from the bin through the first pipe into the nozzle (arrow 6), positioned inside the at least one insect cage, in order to clean the inner surface of the insect cage. During the cleaning process, the cleaning liquid collects debris, such as dead insects and uncollected eggs as described above, that was present in the insect cage. This mixture of cleaning liquid and debris can then be expelled from the inside of the insect cage through the second pipe to for example the bin 120 (direction of arrow 5). In one embodiment, a pump 102, positioned between the bin 120 and the insect cage 101, is configured to deliver cleaning liquid to the interior of the insect cage with at least one of a predetermined flow rate and a predetermined liquid pressure.

An example of such an insect breeding device is the insect breeding device comprising at least one insect cage; a bin for holding a cleaning liquid; a first pipe connected to the bin for receiving the cleaning liquid, wherein the pipe is entering the at least one insect cage through a first opening in the at least one insect cage; a nozzle, coupled to the first pipe, positioned inside the at least one insect cage configured to deliver the cleaning liquid to the interior of the at least one insect cage; and a second pipe, coupled to a second opening in the at least one insect cage, different from the first opening in the at least one insect cage, configured to drain the cleaning liquid and debris remaining from farming insects in the insect cage from the at least one insect cage.

Figure 2A:
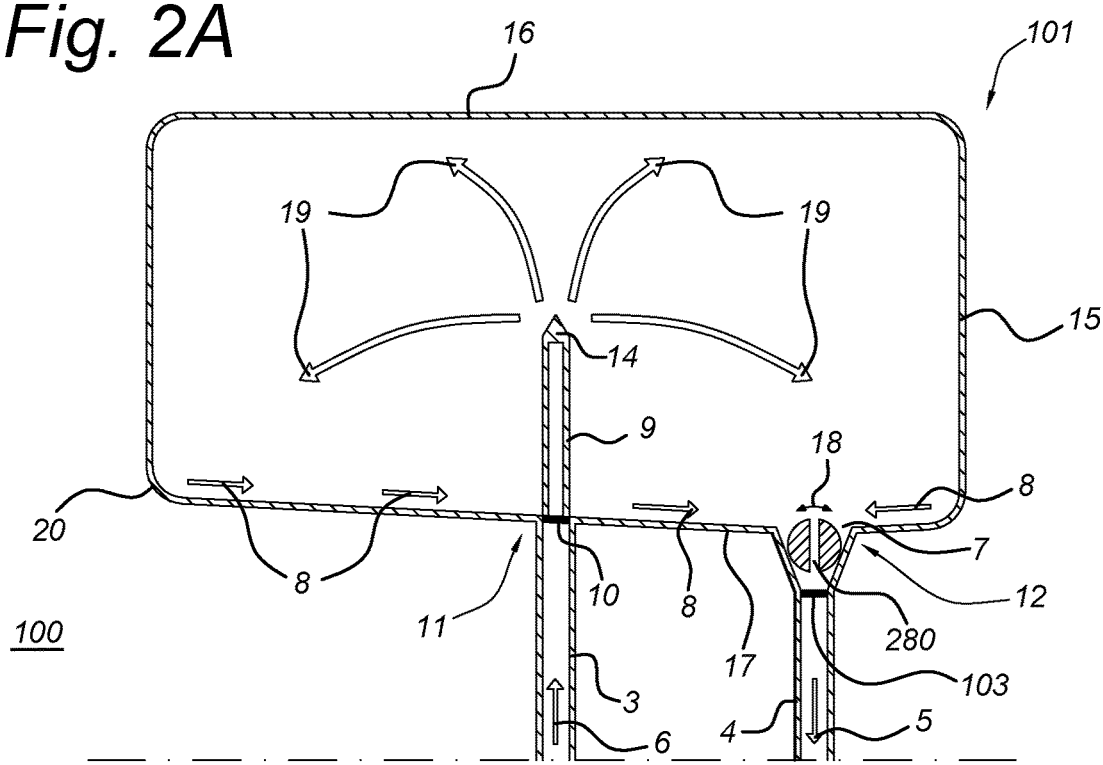
FIG. 2A, B (FIG. 2A, B) illustrates an embodiment of an insect cage of the present invention.
Figure 2B:
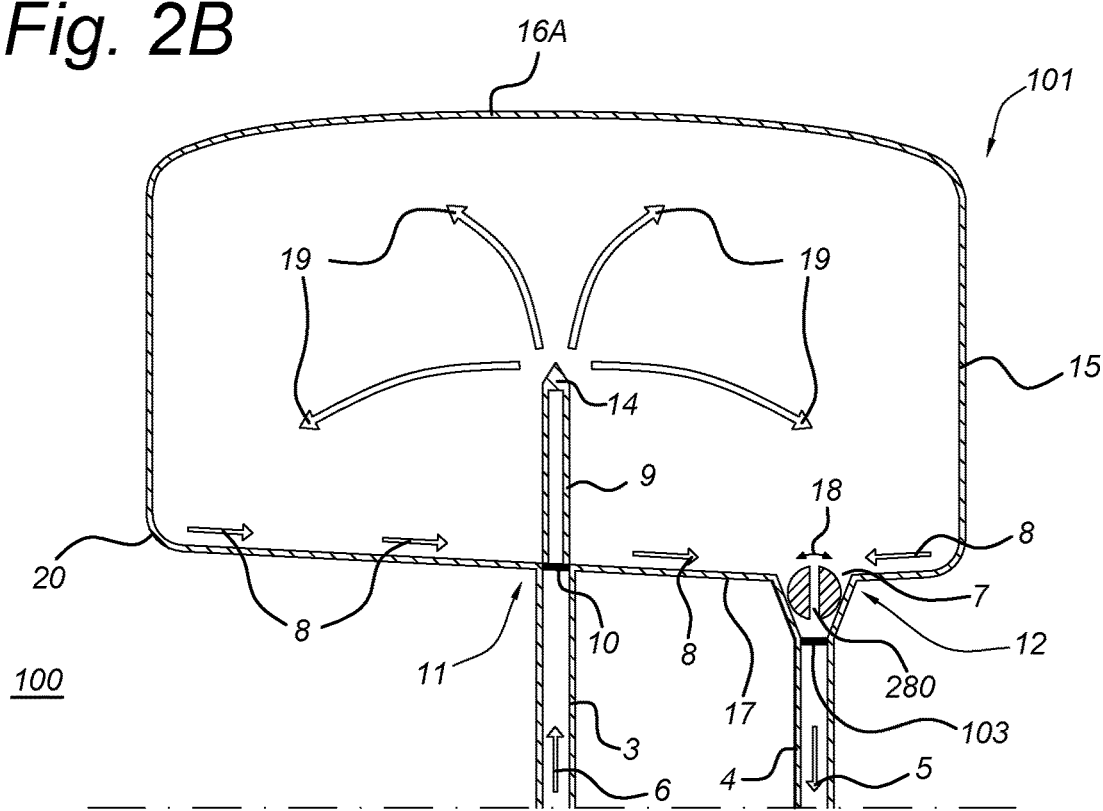

FIG. 2A, B show insect cage 101 in the insect breeding device according to two embodiments of the invention. The insect cage 101 has a closed top wall 16, 16A, wherein the top wall has a flat and non-curved shape (FIG. 2A, top wall 16), or preferably has a concave shape (FIG. 2B, top wall 16A) (seen from the interior of the insect cage). FIG. 2A, B show schematically flows 19 of cleaning liquid so that any remains of the insect colony after death of said colony is removed from the inner surfaces 15 of the round cornered cages 101. Such remains include feces, dead insects, eggs ovipositioned outside the ovisite, pupae exoskeletons, dead pupae, etc. (debris). Due to the concave shape of the top wall 16A (seen from the interior of the insect cage), the cleaning liquid, water for flushing remaining cleaning liquid in the cage, does not adhere as droplets at the surface of the inner side of the top wall 16A. Instead, the curvature of the plastic, i.e. polymer top wall 16, 16A is such that cleaning liquid and water is drained from the inner side of the top wall towards the side walls of the cage, and subsequently drained through the drain and out of the cage. That is to say, cleaning liquid droplets and water droplets can not adhere to the inner side of the top wall, and instead flow over the side walls towards the (tapered) bottom wall and into the drain. This way, liquid does not stay in the cage after the cleaning cycle, and drying of the cage after cleaning is quicker when compared to a top wall occupied by cleaning liquid droplets or water droplets. In addition, the risk for liquid being present after the cleaning cycle is reduced, such that insects are not exposed to droplets of cleaning liquid and/or droplets at a size that may cause insects to become drown in the droplet. Moreover, due to the concave shape of the top wall 16A (seen from the interior of the insect cage), cleaning liquid comprising waste, dirt, insect remains, faeces, etc., is efficiently removed from the interior of the cage, with reduced risk for droplets comprising said waste to be discarded, being present in the cage when the cage is used for breeding insects. The risk for contaminating a new breed of insects is thus reduced by using cleaned cages with concave shaped top wall 16A (FIG. 2B; seen from the interior of the insect cage). In addition, due to the concave shape of the top wall 16A (seen from the interior of the insect cage), gravid female insects are prevented from ovipositioning at the top wall 16A and its respective corners of the insect cages. A further advantage of such concave shape of the top wall is its contribution to the efficiency of the cleaning operation of the insect breeding device.

In this embodiment the cleaning liquid can be flushed through the insect cage 101 after e.g. insects die inside the cage. In one embodiment, the cleaning liquid is water. In another embodiment, the cleaning liquid comprises a mixture of water and at least one detergent. Preferred detergents for application in the cleaning liquid used for cleaning using the insect breeding device are non-foaming detergents, although foaming detergents are also applicable in the cleaning liquid. In an embodiment the cleaning liquid comprises between 0.5% and 10% non-foaming detergent by volume of the cleaning liquid. In one embodiment, the cleaning liquid is an aqueous solution comprising less than 1.5% non-foaming detergent by volume of the total cleaning liquid. In a further embodiment, the cleaning liquid is an aqueous solution comprising about 1.0% non-foaming detergent by volume of the total cleaning liquid.

The fluid nozzle 14 can be a spiral water spray nozzle, a full-cone nozzle, one or two full cone nozzles, a deflector plate nozzle, a solid jet nozzle. The nozzle 14 is for example positioned at the distal end of a pipe 9 connecting the nozzle and pipe 3, relative to the first opening 11 in the bottom wall of the cage 101. The position inside the insect cage is such that in operation the complete surface of the inner side of the insect cage is contacted with the cleaning liquid 19, i.e., expelled at for example a pressure of about 3 bar, for example for about 50 minutes, at a speed of between about 10 liter/minute and 500 liter/minute, preferably between 30 liter/minute and 180 liter/minute, more preferable between 60 liter/minute and 80 liter/minute, such that for example the insect cage is cleaned with a volume of cleaning liquid such as a mixture of water and detergent, of between 500 liter and 25.000 liter, such as for example a preferred volume of about 3.500 liter when the insect cage has an inner volume of about between 100.000 $cm^3$ and 1.000.000 $cm^3$, preferably about 900.000 $cm^3$. In an embodiment, the nozzle is a rotating head, capable of rotating at low rate and expelling less fluid per minute than the spiral nozzle.

Technical details and performance details related to a preferred nozzle for application in the insect breeding device, such as a spiral nozzle or a solid jet nozzle, which is preferred, are:
- Flow rate range: between 60 L/min and 100 L/min at 2.5 bar, preferably about 80 L/min;
- Spray angle: between 240° and 300°, preferably about 270° for a solid nozzle, or between 120° and 90° for a spiral nozzle; and
- Spray pattern: Full cone or solid jets from a sphere.

In one embodiment, the insect breeding device of the present invention comprises a single nozzle 14 positioned centrally in the inner volume of the insect cage. The nozzle is coupled to a rigid pipe or tube 3 for example made of metal or a polymer, said pipe or tube entering the cage inner volume either through the top wall of the insect cage, from above, or through opening 11 in the floor 17 of the insect cage, from below. Alternatively, the pipe or tube enters the insect cage through an opening in a side wall of the cage. Positioning the nozzle in the middle of the insect cage volume contributes to the efficiency of the cleaning. In one embodiment, the insect cage comprises at least two nozzles, preferably two nozzles positioned off center in the inner volume of the insect cage, for example at positions in the floor located between 25% and 75% of the depth of the insect cage. In this arrangement the two nozzles in operation during a cleaning cycle generates a cyclone of washing solution or water near and in the drain.

The insect cage can be provided with at least one, preferably a single floor drain located in the second opening 12. The diameter of the circular drain opening in the floor can be between 2 cm and 14 cm, preferable between 3 cm and 10 cm, more preferably about 5 cm. Preferably, the insect cage has a block shape with rounded corners 20. Sharp edges between the opening of the drain and the floor of the cage are obeyed, as well as the presence of any recess or ridge in the side of the opening. It appears that gravid female insects, e.g. gravid female black soldier flies, are in this embodiment prevented from deposition of their eggs in the opening or close proximity of the opening, since the provision of a perceived shelter, for example under a ridge, in a recess, in the opening below floor level, etc., for the eggs is prevented.

The floor drain is configured such that cleaning the insect cage, does not cause the drain 280 to clog. In an embodiment the drain of the insect cage comprises a ball valve 7, since a ball valve has less tendency to clog by particulates present in the drained fluid. Alternatively, a butterfly valve can be applied.

The drain 280 inside the insect cage is positioned centrally in the floor part of the insect cage. Alternatively, the drain inside the insect cage can be located off center in the floor of the insect cage, such as in a corner. In an embodiment the insect breeding device can be provided with multiple drains in the floor of the insect cage. In a further embodiment, the floor part of the insect cage is tapered, having an amount of slope descending from the location of the side walls of the cage in the direction of the floor drain(s). Herewith, drainage 8 of the cleaning liquid is ensured during a washing cycle. In one embodiment, the insect cage can be provided with least one drainage opening 12, positioned off center in the floor surface. For example, the opening or openings such as two openings for draining fluid during cleaning of the cage is/are located in a portion of the floor of the cage located between 5 cm and 20 cm from the side walls of the cage. When two or more openings for draining the cleaning liquid are provided in the floor of the insect cage, the openings can be evenly spaced in said floor surface. In one embodiment, the insect breeding device further comprises of a second pump 103, positioned between the second opening of the insect cage and the bin 120, the second pump is configured to transport the cleaning liquid and debris from the at least one insect cage 101 to the bin 120.

In one embodiment, the insect breeding device typically flushes the inside of the insect cage with the cleaning liquid exiting from the first opening in the insect cage at a pressure of between 1.5 bar and 6 bar, preferably between 2 bar and 3 bar.

The insect breeding device typically flushes the batches of insect cages for a period between 20 minutes and 120 minutes, preferably between 30 minutes and 90 minutes, more preferably for between 40 minutes and 60 minutes, wherein each batch comprises between 2 and 20 cages, preferably 4 cages. On average, preferably the insect breeding device typically flushes between 5 and 20 cages per hour, such as about 8 to 14 cages per hour, preferably about 11 cages per hour.

In an embodiment of the present invention, the insect cage comprises a first valve 10, coupled to a first opening 11 of the insect cage, configured to open or close the first opening, and a second valve 18, coupled to a second opening of the insect cage, configured to open or close the second opening.

In one embodiment, the insect breeding device comprises a controller 105 connected to the first valve and the second valve and the first pump and the second pump, wherein the controller can switch between a first state and a second state. In the first state the first and second valves 10, 18 are closed and the first and second pumps 102, 103 are switched off. This first state represents when the insect cage does not require cleaning, and it is not possible to deliver or expel cleaning liquid into and from the insect cage. In the second state, the first valve is open and the second valve is open, the first pump is switched on and the second pump is switched on. In the second state the cleaning liquid is delivered into the insect cage and the cleaning liquid, and debris, is flushed out of the insect cage.

In one embodiment, the insect breeding device comprises a heater 104 arranged between the bin 120 and first pump 102. The heater is arranged to heat the cleaning liquid delivered to the first pump at a temperature in the range of 31.5° C. to 32° C.

Figure 3:
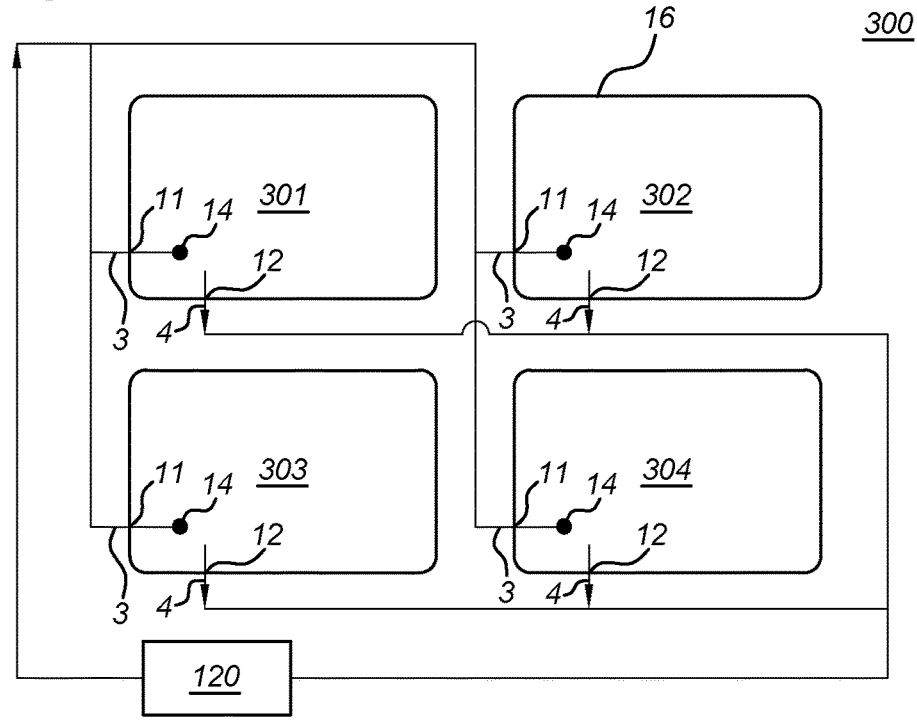
FIG. 3 (FIG. 3) illustrates an embodiment of an insect breeding device comprising of more than one cage.

FIG. 3 shows an insect breeding device 300 provided with four insect cages 301, 302, 303, 304 according to a second embodiment of the invention. All four insect cages are connected to the same bin 120. However, the total number of cages of the insect breeding device is not restricted to four. The insect cages in this embodiment are similar to those as described hereinbefore, for example insect cage 101. The insect cages having a top wall 16, wherein the top wall for example has a concave surface seen from the interior of the insect cage.

Furthermore, the controller is arranged to control the first and second valves of the insect cages and the first and second pump.

The controller can be further arranged to clean one or more cages simultaneously, or in batches, or individually, with reduced reliance on labor and at increased speed during the cleaning step.

In one embodiment, wherein the insect breeding device has a multiple cages, the insect breeding device can have a cleaning capacity of between 2 cages/hour and 50 cages/hour, preferably between 5 cages/hour and 25 cages/hour, more preferably between 8 cages/hour and 16 cages/hour. In one embodiment, the insect breeding device can have a cleaning capacity for batch wisely washing at least 2 cages simultaneously, preferably at least 4 cages simultaneously, more preferably at least 10 cages simultaneously, most preferably at least 20 cages simultaneously.

For example, the insect breeding device may comprise, about one hundred horizontally and vertically stacked insect cages in an insect farming room such as a climate room for breeding insects, and can be cleaned without the need to displace the insect cages for the purpose of cleaning. Typically, the insect breeding device may comprises two-ten insect cages are stacked vertically, and typically tens to hundreds of insect cages are stacked horizontally, such as about 20-500 insect cages.

Typically, stacked insect cages provided with the insect breeding device have round-corners on the inner surface of insect cages (hereafter referred to as "round cornered cages"). Such round cornered cages contribute to preventing gravid female insects from ovipositioning at the corners of the insect cages. An advantage of such round cornered inner cage walls is its contribution to the efficiency of the cleaning operation of the insect breeding device.

The round cornered cages that are provided with the insect breeding device are preferably produced by rotation molding. Rotation molding provides cages with an inner surface of the side walls, top and floor that is particularly smooth. Such smooth surfaces contribute to the cleaning efficiency of the insect breeding device.

In one embodiment, the round cornered cages provided with the breeding device of the invention are made of a polymer or a polymer blend, preferably the cages are made of a polymer blend comprising polyethylene. In one embodiment, the round cornered cages provided with the breeding device of the invention are made of polyethylene. In one embodiment, said round cornered cages are made by rotation molding a blend of polyethylene, according to the invention. In one embodiment, said round cornered cages are made by rotation molding medium density polyethylene, according to the invention. In one embodiment, the round cornered cages provided with the breeding device of the invention are made of polypropylene.

Typically, a plurality of insect cages provided with the insect breeding device of the present invention have an inner size suitable for farming between 500 and 50.000 adult insects, such as between 1.000 and 20.000 adult insects. Typically, the round cornered cages for farming adult insects such as black soldier flies and for collecting the eggs derived therefrom, have inner dimensions of between 30 cm and 300 cm (width), between 50 cm and 400 cm (depth), and between 10 cm and 200 cm (height), for example between 30 cm and 220 cm (width), between 50 cm and 300 cm (depth), and between 10 cm and 150 cm (height), or for example between 30 cm and 150 cm (width), between 50 cm and 200 cm (depth), and between 10 cm and 100 cm (height). Preferably, such round cornered cages provided with the insect breeding device of the present invention are substantially block shaped, typically with the following dimensions: about 120 cm (width), about 50 cm (height), 170 cm (depth), or for example about 160 cm (width), about 90 cm (height), 220 cm (depth). Preferred is a cage with a width of about 110 cm, a height of about 70 cm and a depth of about 160 cm, or for example a width of about 140 cm, a height of about 80 cm and a depth of about 200 cm.

Conventional cleaning of the insect cages one by one would require about between 6 minutes up to 12 minutes, and typically about 10 minutes on average of labor. Applying the automated and controllable insect breeding device of the present invention reduces the required time for cleaning a single insect cage to between 40 minutes and 60 minutes, on average, for cleaning for example between 4 and 20 cages simultaneously. Furthermore, the insect breeding device can wash multiple cages simultaneously, thus there is a significant gain in time required for cleaning cages when compared to individually cleaning cages by hand.

Conventional cleaning of insect cages by hand requires about between 150 liters and 250 liters of cleaning liquid, i.e. water comprising at least one detergent, preferably non-foaming detergent, or water per cage, and about 200 liters on average per insect cage. Preferably, the non-foaming detergent is for example Ecofoam, preferably about 1.0% Ecofoam by volume of the total cleaning liquid. Applying the insect breeding device of the present invention reduces the amount of cleaning liquid or water required to clean a single cage to between about 60 liters and 150 liters, such as for example a preferred volume of between about 70 liters and 140 liters per insect cage, more preferably between 80 liters per insect cage and 130 liters per insect cage according to the invention, such as about 90 liters per insect cage or about 110 liters per insect cage. Typically, according to the invention, the nozzle such as a spiral nozzle head, delivers about 60 liters per minute to 90 liters per minute water or cleaning liquid for a period of about one hour, preferably about 80 liters per minute according to the invention.

Figure 4:
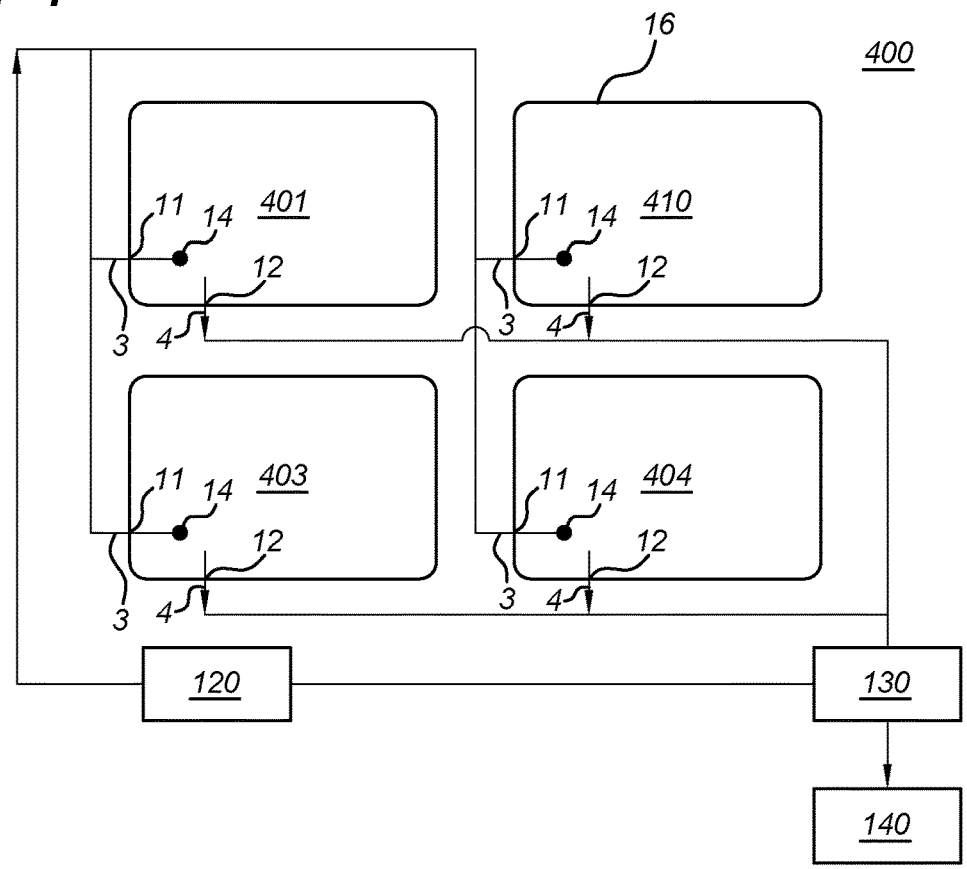
FIG. 4 (FIG. 4) illustrates an embodiment of an insect breeding device.

FIG. 4, shows an insect breeding device 400 with four insect cages 401, 410, 403, 404 according to a third embodiment of the invention. The insect cages in this embodiment are similar to those as described hereinbefore, for example insect cages 101, 301-304. Furthermore, in this embodiment at least part of the cleaning liquid used for cleaning the insect cage with the insect breeding device is re-used.

Preferably, between 10% and 100% of the cleaning liquid or water is re-used, for example between 25% and 80%. In one embodiment, for example 100% of the cleaning liquid is re-used for cleaning between 28 and 136 cages, such as about 64 cages, said cages cleaned in batches of 4 cages simultaneously, and for example subsequently 100% of water is re-used for rinsing the between 28 and 136 cages, such as about 64 cages, said cages again cleaned in batches of 4 cages simultaneously. For the purpose of recycling water or cleaning liquid, the insect breeding device 400 further comprises a liquid clearance device 130. The liquid clearance device 130 comprises a solid particle separation member such as a filter, a mesh, a screen, preferably a mesh, and/or such as a centrifugation arrangement. In one embodiment, the filter of the insect breeding device of the present invention comprises an angled sieve for separating liquids after cleaning from particulates. Such an angled sieve is a sieve that is tilted at an angle alpha relative to the horizontal, such that fluid such as the water or the cleaning liquid collected after cleaning the insect cage passes through the sieve and particles remain on top of the sieve, and said particles slide down the angular slope of the sieve towards for example a debris receptacle 140.

After clearing the used water or cleaning liquid that was collected after cleaning an insect cage, from solid particles originating for example from feces, uncollected eggs, dead insects, pupae remains, etc., said cleared fluid is at least in part reintroduced in the cage washing system, for re-use in a subsequent cleaning cycle. Optionally, the water or cleaning liquid cleared from particulates is first further cleaned from e.g. dissolved or dispersed contaminations, before being re-introduced in a cleaning cycle. Such a cleaning step is for example a ramp sieve whereby exuvi, etc. are sieved on a ramp and slide to a collection area while the cleaning liquid falls through the sieve and is re-used. Such a cleaning step comprising separating solution from solid particles is essential when water or cleaning liquid is applied during a cleaning cycle with a first batch of cages using the insect cage washer of the invention, and is re-used in a cleaning cycle with a further batch of cages. Optionally, cleaning liquid or water cleared after use in a cleaning cycle, is first stored before being applied in a next cleaning step. Thus, optionally, the insect breeding device of the present invention further comprises a liquid tank.

One of the many advantages of the insect breeding device of the present invention is the safety that is provided to workers involved in the farming of insects including cleaning of insect cages between two subsequent cycles of breeding, with regard to the reduced risk of contact with irritants. Since the insect breeding device is a closed system, exposure of detergents present in the cleaning liquid to the environment is limited, contributing to a safe working environment in the insect farming room.

Before an insect cage is used in a first or subsequent round of an insect breeding cycle starting from the pupae stage up to death of the adult insect after mating and the gravid female insects having ovipositioned, the applied insect cage preferably has a dry inner surface cleared from droplets of fluid such as water.

Figure 5:
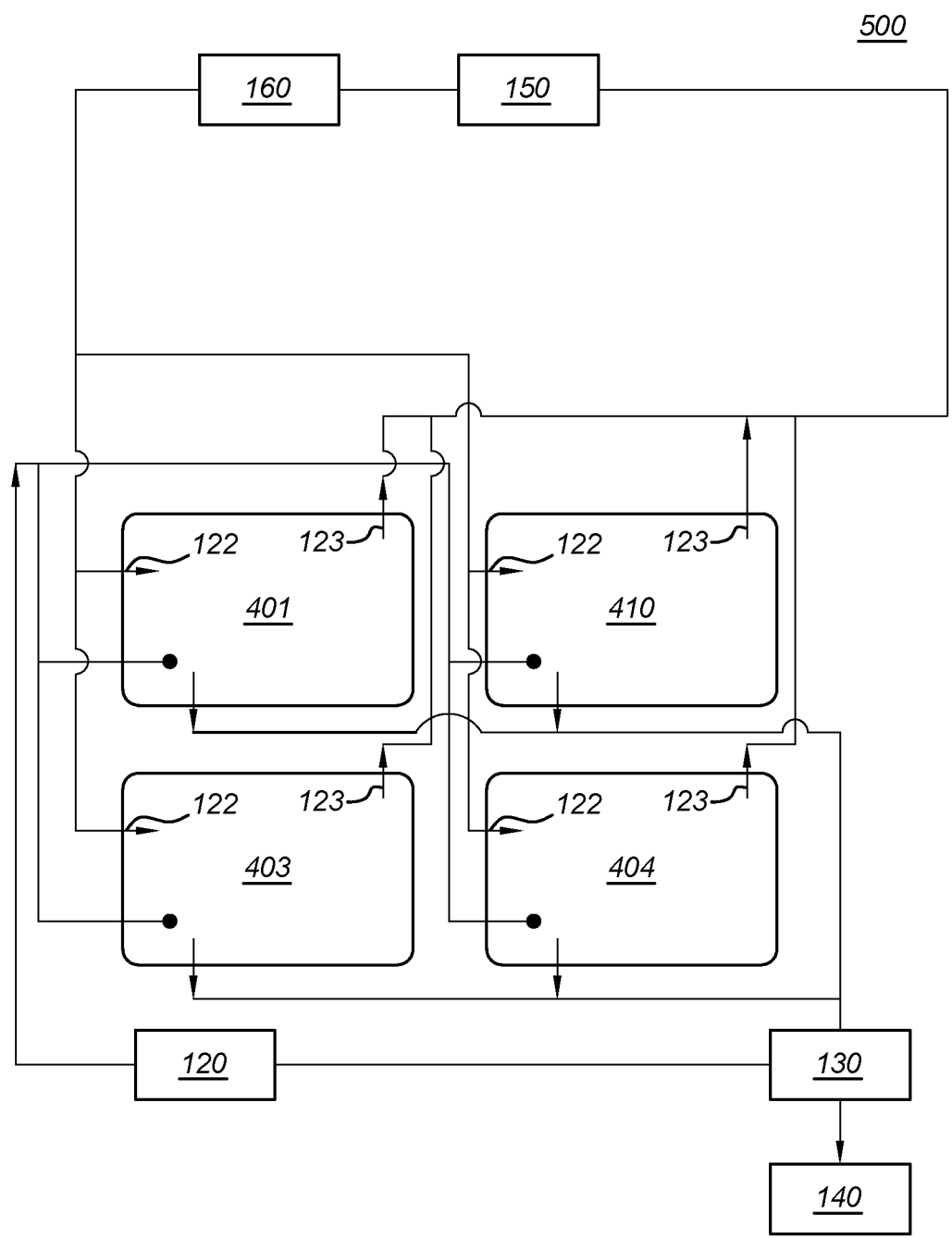
FIG. 5 (FIG. 5) illustrates an embodiment of an insect breeding device with a gas drying apparatus.

FIG. 5, shows the insect breeding device 500 of a third embodiment according to the invention. The insect cages in this embodiment are similar to those as described hereinbefore, for example insect cage 101, 301-304, 401, 403, 404, 410. The insect breeding device further comprises a gas drying apparatus drying the interior of each insect cage after the insect cages have been cleaned. Preferably, the interior of the insect cages is dried with air after cleaning of the insect cages. In an embodiment the insect breeding device 500 further comprises of a ventilator 150 and optionally an air heater 160. The ventilator 150 generates a gas flow, where the gas is then optionally heated at the heater 160. The gas or the heated gas is then transferred through a third pipe to supply air to the insect cages 401, 403, 404, 410 through a third opening 122 of the insect cage. A fourth opening 123 of the insect cage is used to return the gas to the ventilator 150.

In one embodiment, the insect cage further comprises of a third valve coupled to the third opening configured to open or close the third opening, and a fourth valve, coupled to the fourth opening, configured to open or close the fourth opening.

Figure 6:
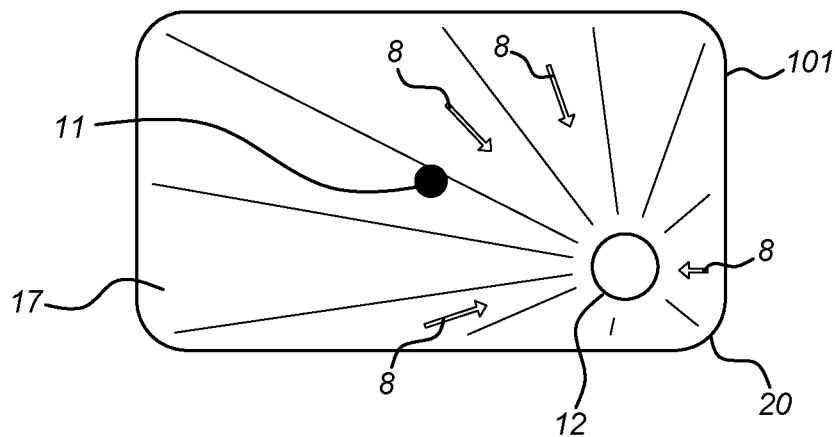
FIG. 6 (FIG. 6) illustrates an embodiment of a bottom side at the interior of an insect cage.

FIG. 6 shows an interior bottom floor 17 of the insect cage 101, which floor is a tapered floor 17. The insect cage has a closed top wall 16 (not shown), such as a top wall with a concave surface (seen from the interior of the insect cage). The floor comprises the opening 11, here located essentially in the center of the floor, and the second opening 12, here essentially located at or near a rounded corner 20 of the insect cage, in the bottom floor 17. Drainage of a fluid, such as the drainage 8 of the cleaning liquid comprising debris is directed from all sides and locations inside the insect cage, along the tapered floor surface towards the corner near which the second opening 12 is located in the bottom floor 17. This interior bottom floor 17 can also be provided in the insect cages 301-304, 401, 403, 404, 410 in the embodiments described herein before.

Figure 7A:
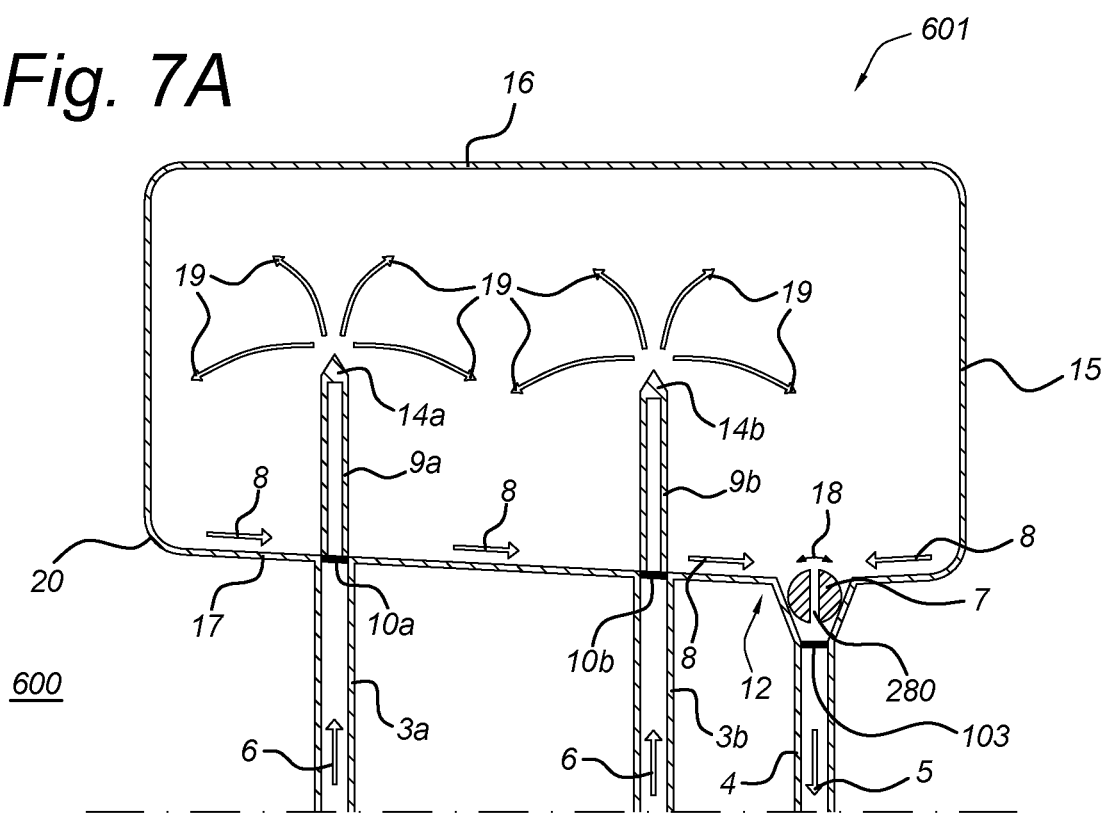
FIG. 7A, B (FIG. 7A, B) illustrates an embodiment of an insect cage.
Figure 7B:
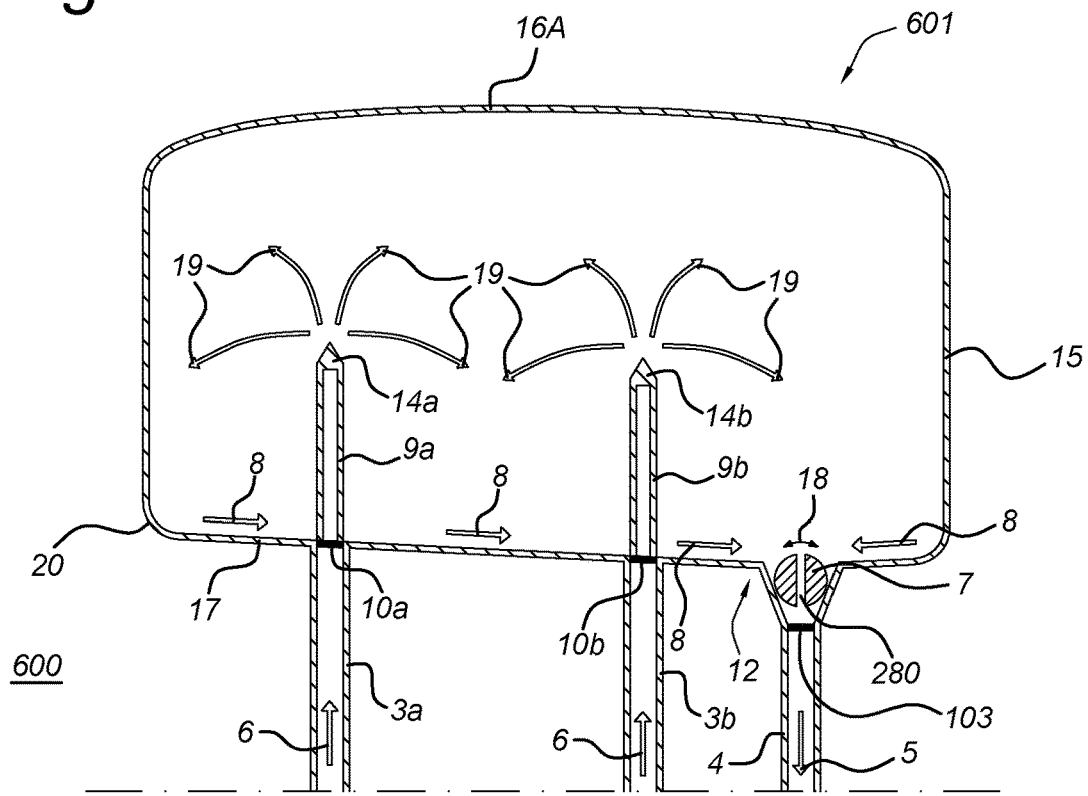

FIG. 7A, B show the insect breeding device 600 of a fourth and a further embodiment according to the invention, comprising insect cage 601. The insect breeding devices encompass at least an insect cage 601, said cage provided with two nozzles 14a and 14b, connected to pipes 3a and 3b through pipes 9a and 9b, respectively, the pipes 3a and 3b further provided with a valve 10a and 10b, respectively. The top wall 16A of the insect cage is for example a wall having a concave surface (FIG. 7B; seen from the interior of the insect cage), which is the preferred embodiment. Alternatively, the top wall 16 of the insect cage is for example a wall having a flat, non-curved surface (FIG. 7A; seen from the interior of the insect cage).

Figure 8A:
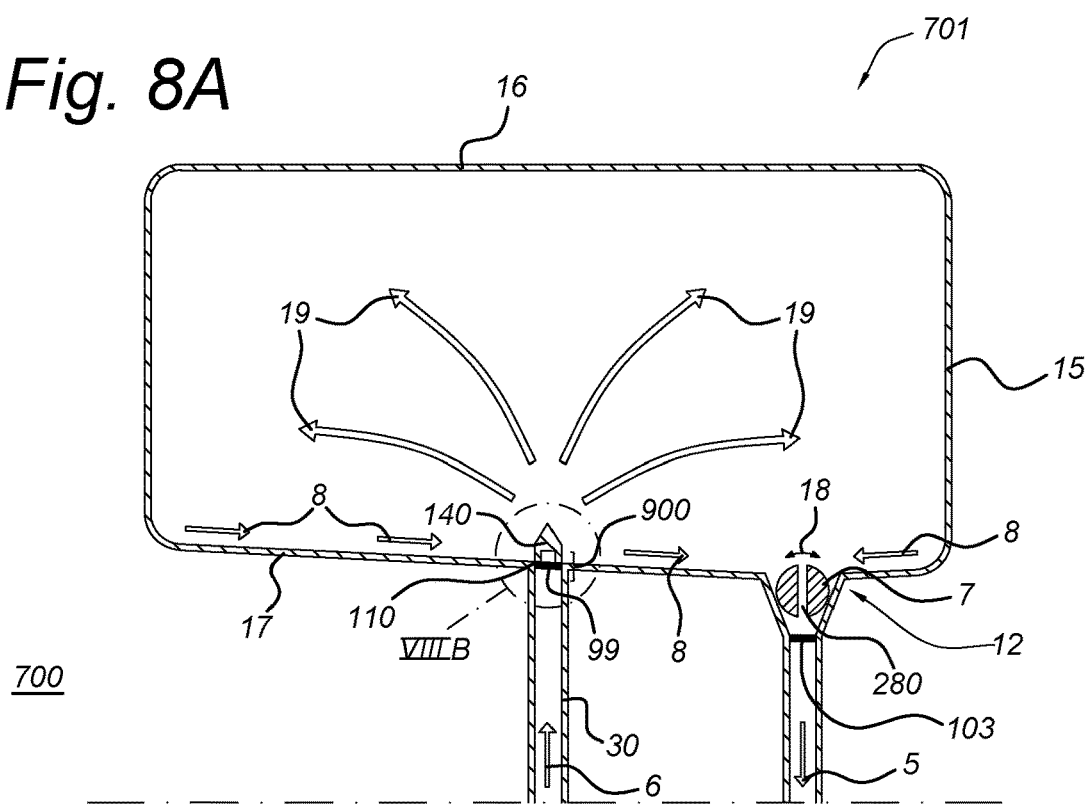
FIG. 8A (FIG. 8A) illustrates an embodiment of an insect cage.
Figure 8B:
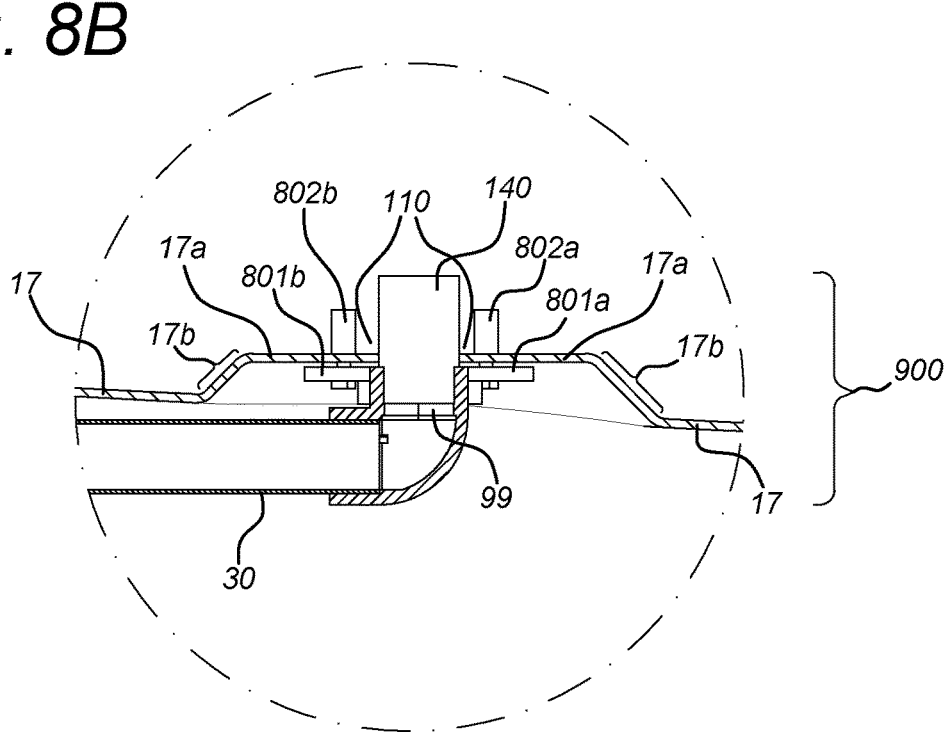
FIG. 8B (FIG. 8B) illustrates an excerpt of the insect cage of FIG. 8A, zoomed in on a nozzle entering the interior of the insect cage.

FIG. 8A shows the insect breeding device 700 of a fifth embodiment according to the invention, comprising at least a cage 701. The insect breeding device comprises insect cage 701, said insect cage encompassing a nozzle 140 located at or near the surface of the bottom 17 at the inner side of the insect cage. The nozzle 140 is connected to pipe 30 through a connector 900 which embraces opening 110 in the bottom floor 17. The pipe 30 comprises valve 99 located in or near the opening 110. Cleaning liquid enters insect cage 701 in the direction 6 through pipe 30 and schematically flows 19 of cleaning liquid inside the insect cage are indicated. FIG. 8B shows an example of the connection between the nozzle 140 in the interior of the insect cage 701 and the pipe 30 connected to a reservoir of cleaning liquid (not shown). The connection is through connector 900. The floor 17 of the insect cage 701 has a protruded portion surrounding the opening 110. The protrusion in floor 17 comprises a portion 17b extending diagonally and upwardly in the direction of opening 110, relative to the main surface of the (tapered) floor 17 of the insect cage. The protrusion in floor 17 further comprises protruded portion 17a surrounding opening 110, and horizontally oriented. The portion 17b connects the main surface portion of floor 17 with the protruded portion 17a surrounding opening 110. Protruded portion 17a comprises one or more through-holes. The connector 900 comprises flanges 801a, 801b provided with a through-hole in communication with the through-hole(s) in protruded portion 17a of floor 17. The connector 900 connects pipe 30 and nozzle 140 by bolds 802a, 802b, provided through the through-holes in the protruded portion 17a of the floor and the through-holes in the flans 801a, 801b of the connector 900. This arrangement provides, a smooth floor 17, comprising nozzle 140, without presence of a ridge, a cavity, an edge, a ledge, etc., under which otherwise debris may accumulate, and/or under which otherwise insects such as ovipositioning black soldier flies may oviposite, i.e. lay eggs at undesired locations in the insect cage. That is to say, the connector 900 provided for a smooth inner surface of the insect cage, preventing accumulation of debris or eggs deposited at undesired locations. The nozzle 140 is for example alternatively positioned at the distal end of a pipe 9 connecting the nozzle and pipe 30, relative to the first opening 110 in the bottom wall of the cage 701. Then, the connector 900 connects pipe 30 and pipe 9.

Figure 9A:
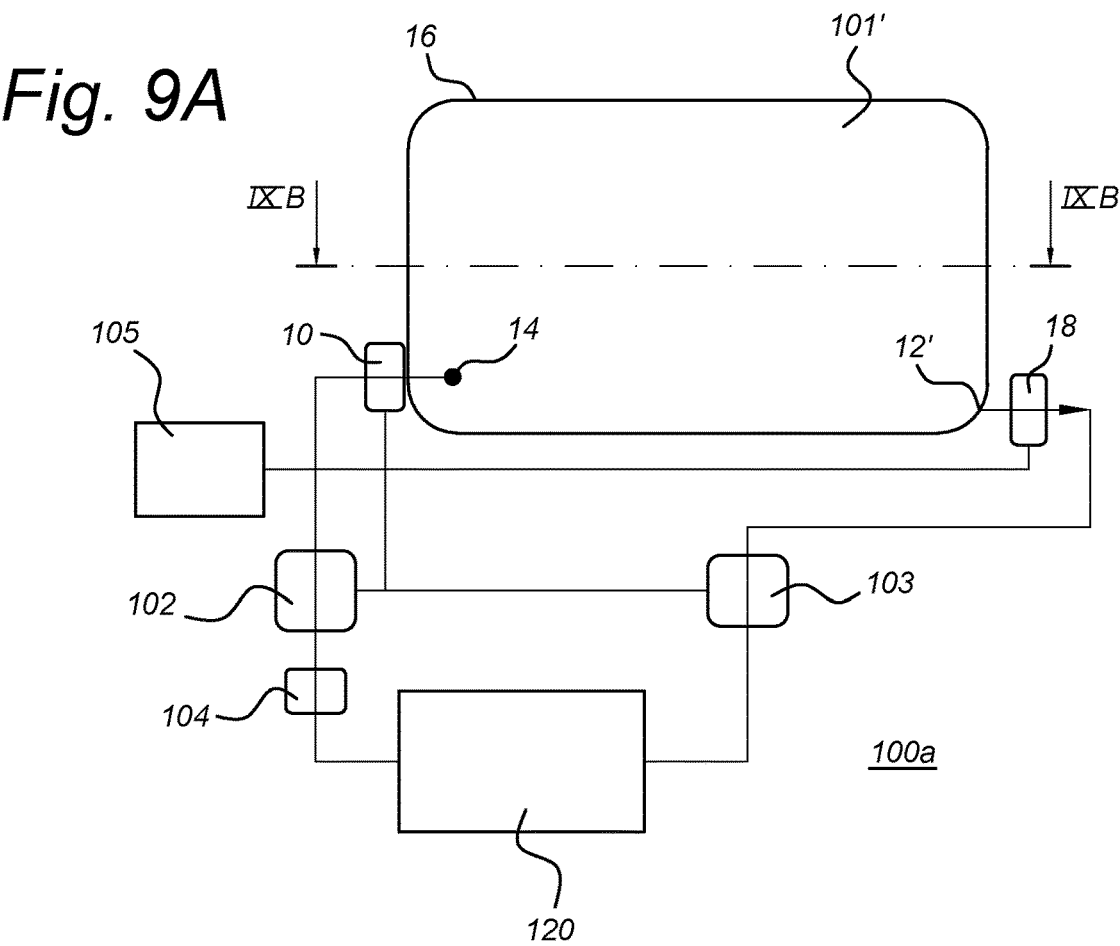
FIG. 9A (FIG. 9A) illustrates an embodiment of an insect breeding device comprising an insect cage of the present invention, with the second opening 12' in the insect cage located in a side wall of the insect cage in the portion of said side wall that connects with the bottom floor of the insect cage.
Figure 9B:
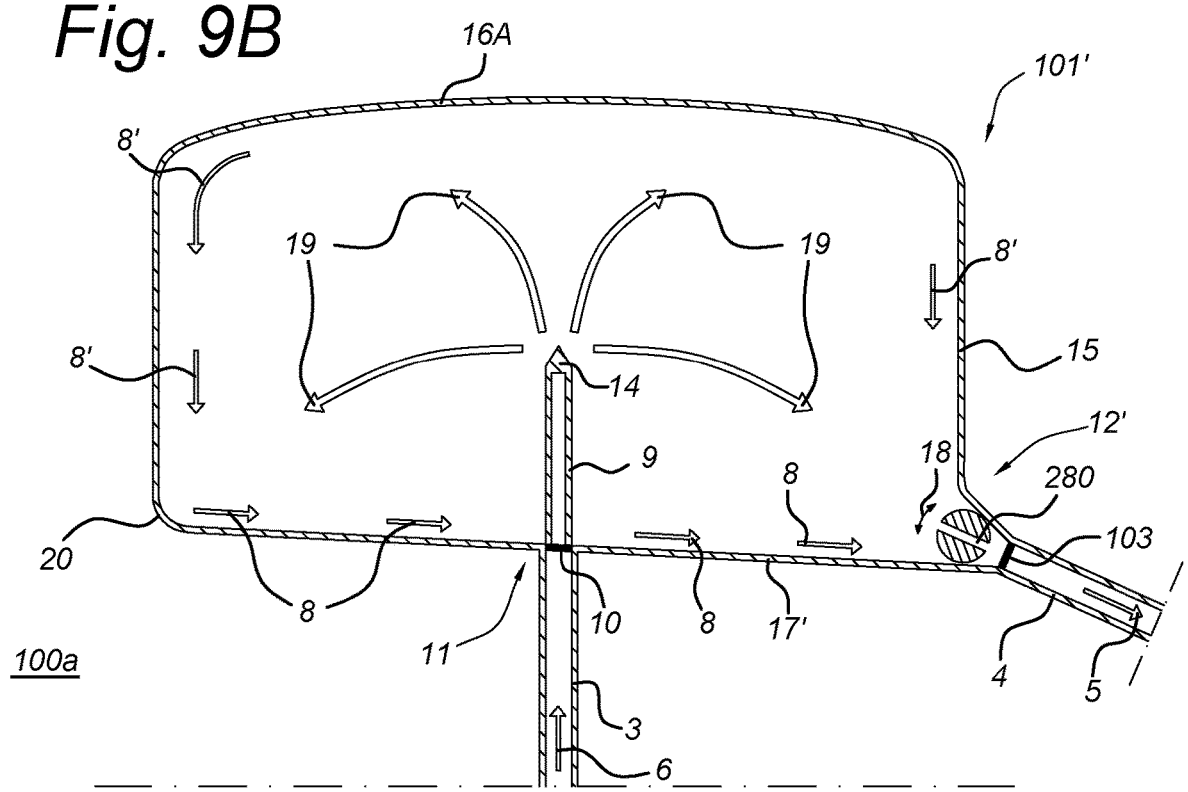
FIG. 9B (FIG. 9B) illustrates an embodiment of an insect cage with the second opening 12' in the insect cage located in a side wall of the insect cage in the portion of said side wall that connects with the bottom floor of the insect cage.
Figure 9C:
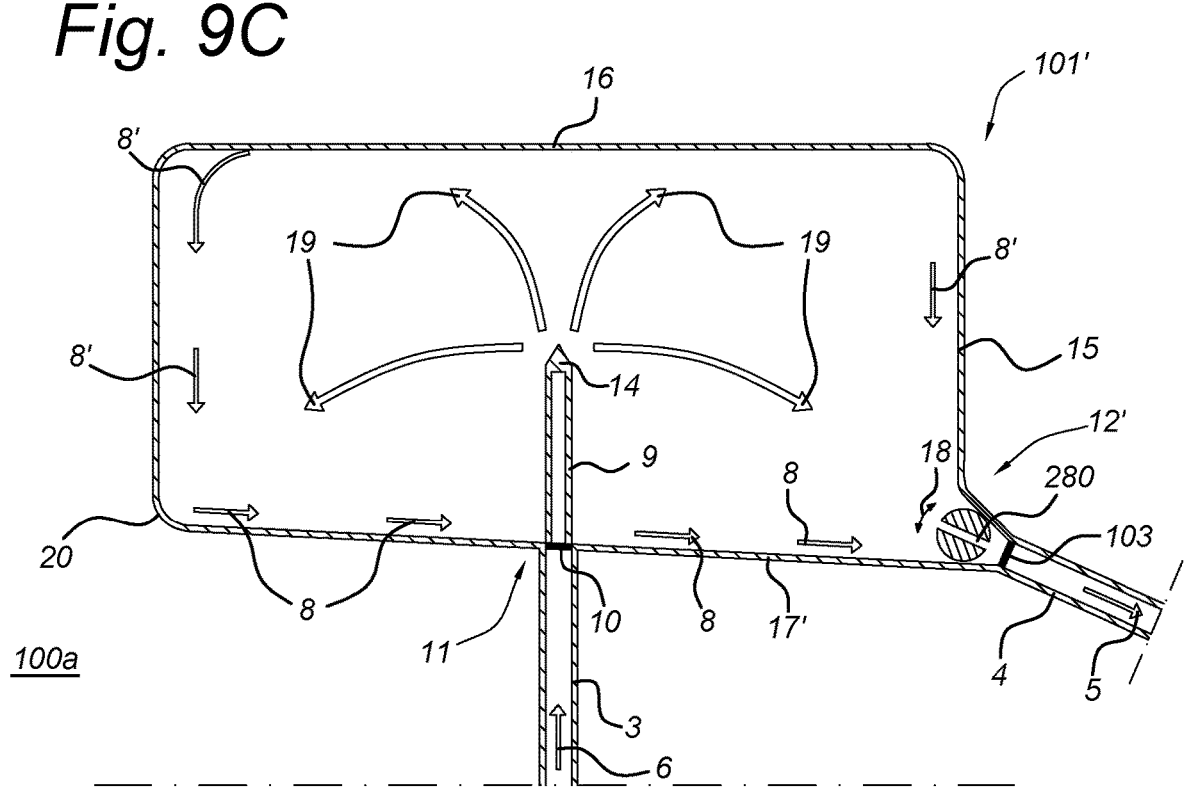
FIG. 9C (FIG. 9C) illustrates an embodiment of an insect cage with the second opening 12' in the insect cage located in a side wall of the insect cage in the portion of said side wall that connects with the bottom floor of the insect cage; the top wall 16A of the insect cage has a concave surface, seen from the interior side of the insect cage.
Figure 9D:
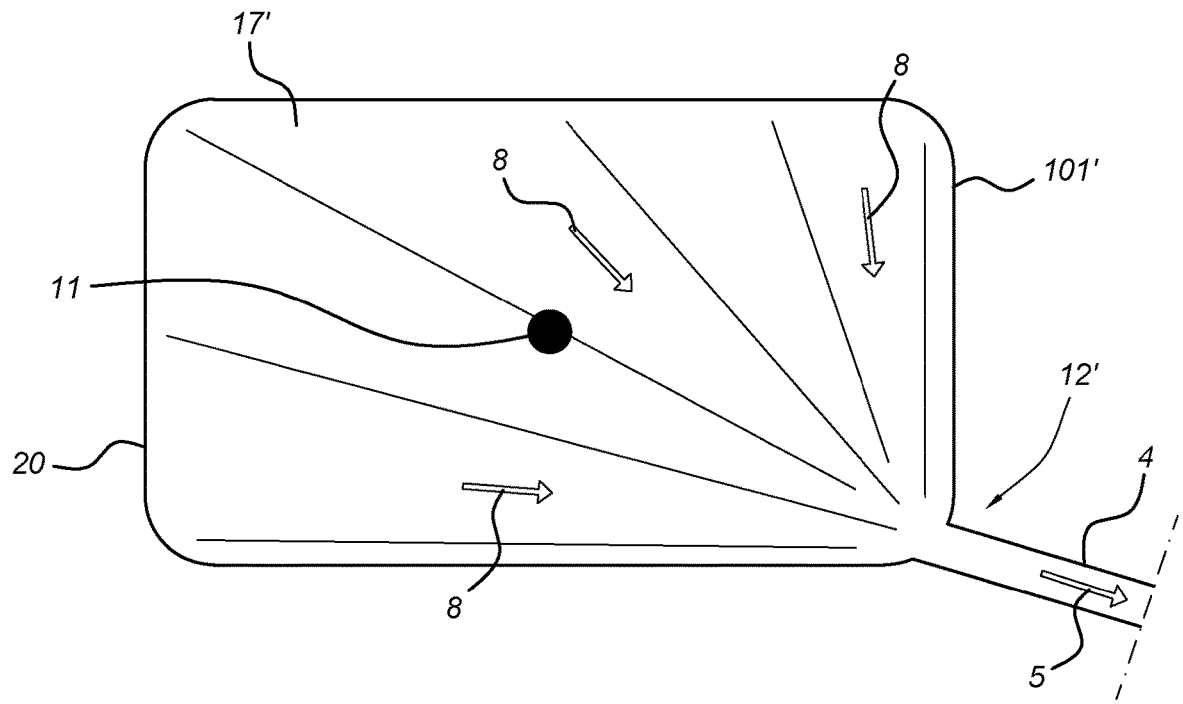
FIG. 9D (FIG. 9D) illustrates an embodiment of a bottom side at the interior of an insect cage, wherein the insect cage comprises a second opening 12' in the insect cage located in a side wall of the insect cage in the portion of said side wall that connects with the bottom floor of the insect cage.

FIG. 9A and FIG. 9B and FIG. 9B and FIG. 9D show the insect breeding device 100a according to a sixth and a further embodiment of the present invention. The insect breeding device comprises an insect cage 101' with a bin 120 for holding cleaning liquid. A pipe 3 is connected from the bin 120 to the first opening 11 of the insect cage 101'. A nozzle 14, coupled to the first pipe 3, is positioned inside the insect cage and is configured to deliver cleaning liquid to the interior of the insect cage. A second pipe 4 connects the second opening 12' of the insect cage 101' to the bin 120. The top wall 16A of the insect cage is for example a wall having a concave surface (FIG. 9B; seen from the interior of the insect cage), which is the preferred embodiment. Alternatively, the top wall 16 of the insect cage is for example a wall having a flat, non-curved surface (FIG. 9C; seen from the interior of the insect cage).

The cleaning liquid flows from the bin through the first pipe into the nozzle (arrow 6), positioned inside the at least one insect cage, in order to clean the inner surface of the insect cage. During the cleaning process, the cleaning liquid collects debris, such as dead insects and uncollected eggs as described above, that was present in the insect cage. This mixture of cleaning liquid and debris can then be expelled from the inside of the insect cage through the second pipe to for example the bin 120 (direction of arrow 5). In one embodiment, a pump 102, positioned between the bin 120 and the insect cage 101', is configured to deliver cleaning liquid to the interior of the insect cage with at least one of a predetermined flow rate and a predetermined liquid pressure.

An example of such an insect breeding device is the insect breeding device comprising at least one insect cage; a bin for holding a cleaning liquid; a first pipe connected to the bin for receiving the cleaning liquid, wherein the pipe is entering the at least one insect cage through a first opening in the at least one insect cage; a nozzle, coupled to the first pipe, positioned inside the at least one insect cage configured to deliver the cleaning liquid to the interior of the at least one insect cage; and a second pipe, coupled to a second opening in the at least one insect cage, different from the first opening in the at least one insect cage, the second opening 12' located in a side wall of the insect cage in the side wall portion in proximity with the bottom floor 17', such that the second opening is located at the lowest point of the insect cage, relative to the horizontal when the insect cage is oriented with the side walls directed vertically, the second opening 12' configured to drain the cleaning liquid and debris remaining from farming insects in the insect cage from the at least one insect cage. The top wall 16A of the insect cage 101' has a concave surface (FIG. 9B; seen from the interior of the insect cage) such that cleaning liquid or water sprayed or condensed onto said concave surface at the interior of the insect cage, does not adhere to the insect cage interior surface, but instead flows over the concave surface towards the side walls of the insect cage, then over the (tapered) floor bottom 17' towards the draining second opening 12' located at the bottom portion of a side wall of the cage, such that liquid flowing over the floor bottom 17' is directed to the lowest point of the interior of the insect cage, i.e. the opening 12'. Drainage of a fluid, such as the drainage 8 and 8' of the cleaning liquid comprising debris is directed from all sides and locations inside the insect cage, along the tapered floor surface towards the corner near which the second opening 12' is located in the side wall where said side wall connects with the bottom floor 17'. In addition, due to the concave shape of the top wall 16A (seen from the interior of the insect cage), gravid female insects are prevented from ovipositioning at the top wall 16A and in its respective corners of the insect cages. A further advantage of such concave shape of the top wall is its contribution to the efficiency of the cleaning operation of the insect breeding device.

FIG. 9D shows an interior bottom floor 17' of the insect cage 101, which floor is a tapered floor 17'. The insect cage has a closed top wall 16, 16A (not shown), such as a top wall with a concave surface 16A (FIG. 9B; seen from the interior of the insect cage) which is the preferred embodiment, or with an essentially flat, non-curved surface 16 (FIG. 9C; seen from the interior of the insect cage). The floor comprises the opening 11, here located essentially in the center of the floor, and the second opening 12', here essentially located at or near a rounded corner of the insect cage, where the bottom floor 17' and a side wall intersect. Drainage of a fluid, such as the drainage 8 of the cleaning liquid comprising debris is directed from all sides and locations inside the insect cage, along the tapered floor surface towards the corner near which the second opening 12' is located in the bottom floor 17'. This interior bottom floor 17' can also be provided in the insect cages 301-304, 401, 403, 404, 410 in the embodiments described herein before.

Figure 10:
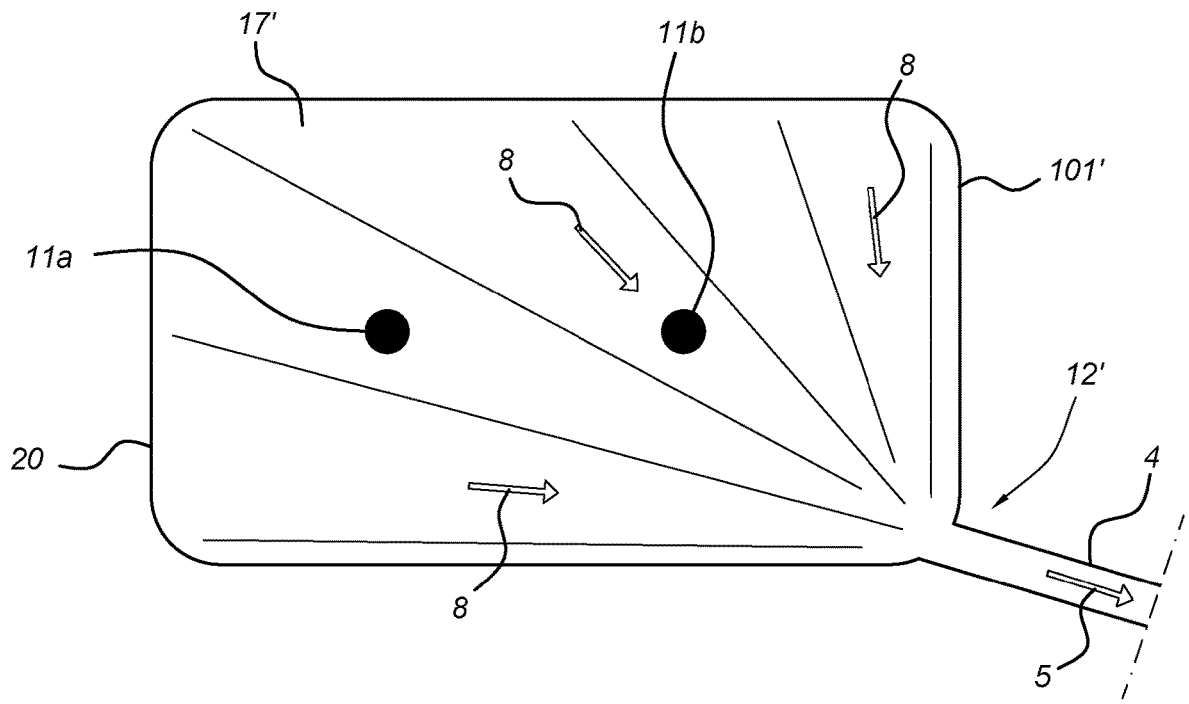
FIG. 10 (FIG. 10) illustrates an embodiment of a bottom side at the interior of an insect cage, wherein the insect cage comprises a second opening 12' in the insect cage located in a side wall of the insect cage in the portion of said side wall that connects with the bottom floor of the insect cage.

FIG. 10 shows an interior bottom floor 17' of an insect cage 101', which floor is a tapered floor 17'. The insect cage has a closed top wall 16, 16A (not shown), such as a top wall 16A with a concave surface (seen from the interior of the insect cage) which is the preferred embodiment, or with an essentially flat, non-curved surface 16 (seen from the interior of the insect cage). The floor is provided with two openings 11a and 11b, here located off-center of the floor 17', and the second opening 12', here essentially located at or near a rounded corner 20 of the insect cage, in a side wall of the insect cage, and at the floor 17', where the floor 17' and the side wall intersect. Drainage of a fluid, such as the drainage 8 and 8' of the cleaning liquid comprising debris is directed from all sides and locations inside the insect cage, along the tapered floor surface towards the corner near which the second opening 12' is located in the side wall where the side wall intersects with the bottom floor 17'. This interior bottom floor 17' combined with the draining second opening 12' located in as side wall can also be provided in the insect cages 301-304, 401, 403, 404, 410 in the embodiments described herein before, wherein the second opening 12 is then replaced by second opening 12'.

The invention can be summarized as follows:

I. Provision of an insect breeding device 100, 100a, 300 400, 500, 600, 700 comprising
at least one insect cage 101, 101', 301, 401, 601, 701, the insect cage having a bottom floor 17, 17', side walls and a top wall 16, 16A, wherein the top wall 16A has a concave surface, seen from the interior side of the insect cage;
a bin 120 for holding a cleaning liquid;

a first pipe 3 connected to the bin 120 for receiving the cleaning liquid, wherein the pipe 3 is entering the at least one insect cage 101, 301, 401, 601, 701 through a first opening 11, 11A, 11B, 110 in the at least one insect cage;

a nozzle 14, coupled to the first pipe 3, positioned inside the at least one insect cage 101, 101', 301, 401, 601, 701 configured to deliver the cleaning liquid to the interior of the at least one insect cage 101, 101', 301, 401, 601, 701; and a second pipe 4, coupled to a second opening 12, 12' in the at least one insect cage, different from the first opening 11, 11A, 11B, 110 in the at least one insect cage 101, 101', 301, 401, 601, 701, configured to drain the cleaning liquid and debris remaining from farming insects in the insect cage from the at least one insect cage 101, 101', 301, 401, 601, 701.

II. Provision of an insect breeding device 100, 100a, 300 400, 500, 600, 700 comprising at least one insect cage 101, 101', 301, 401, 601, 701, the insect cage having a bottom floor 17, 17', side walls and a top wall 16, 16A;

a bin 120 for holding a cleaning liquid;

a first pipe 3 connected to the bin 120 for receiving the cleaning liquid, wherein the pipe 3 is entering the at least one insect cage 101, 301, 401, 601, 701 through a first opening 11, 11A, 11B, 110 in the at least one insect cage;

a nozzle 14, coupled to the first pipe 3, positioned inside the at least one insect cage 101, 101', 301, 401, 601, 701 configured to deliver the cleaning liquid to the interior of the at least one insect cage 101, 101', 301, 401, 601, 701; and a second pipe 4, coupled to a second opening 12, 12' in the at least one insect cage, different from the first opening 11, 11A, 11B, 110 in the at least one insect cage 101, 101', 301, 401, 601, 701, configured to drain the cleaning liquid and debris remaining from farming insects in the insect cage from the at least one insect cage 101, 101', 301, 401, 601, 701, wherein the second opening 12, 12' of the at least one insect cage 101, 101', 301, 401, 601, 701 is located in the bottom floor 17, 17' of the insect cage, or is located in a side wall of the insect cage, in a portion of said side wall where the bottom floor 17, 17' and the side wall provided with the second opening 12' intersect, such that the second opening 12, 12' is located at the lowest point of the insect cage relative to the horizontal when the side wall of the insect cage is directed vertically.

The insect breeding device 100, 100a, 300 400, 500, 600, 700 according to the invention further may comprise a gas drying apparatus provided with a ventilator 150 for generating a gas flow; a third pipe coupled to a third opening 122 of the insect cage 101, 101', 301, 401, 601, 701 for transporting the gas flow inside the at least one insect cage 101, 101', 301, 401, 601, 701, and a fourth opening 123 of the insect cage 101, 101', 301, 401, 601, 701 for releasing the gas out of the at least one insect cage, wherein the insect breeding device optionally further comprises a heater 160 for heating the generated gas flow.

Due to the provision of the insect breeding device of the invention, operating the insect breeding device of the invention now allows for large scale industrial insect farming, e.g. insect breeding, wherein for example the insect breeding device 100, 100a, 300 400, 500, 600, 700 according to the invention comprises a stack of insect cages of length (l) times height (h) times breadth (b) wherein l, h and b run from 2 to 500 (l) cages, from 2 to 20 (h) cages, and from 1 to 200 (b) cages. Typically such as stack of cages encompasses 100×10×50 (l×h×b) insect cages.

While the invention has been described in terms of several embodiments, it is contemplated that alternatives, modifications, permutations and equivalents thereof will become apparent to one having ordinary skill in the art upon reading the specification and upon study of the drawings. The invention is not limited in any way to the illustrated embodiments. Changes can be made without departing from the scope which is defined by the appended claims. The embodiments of the invention described herein can operate in combination and cooperation, unless specified otherwise.

The invention claimed is:

1. An insect breeding device comprising:
   at least one insect cage, the insect cage comprising a bottom floor, side walls and a top wall;
   a bin for holding a cleaning liquid;
   a first pipe connected to the bin for receiving the cleaning liquid, wherein the first pipe enters a first insect cage from the at least one insect cage through a first opening in the first insect cage;
   a nozzle, coupled to the first pipe, positioned inside the first insect cage configured to deliver the cleaning liquid to the interior of the first insect cage;
   a second pipe, coupled to a second opening in the first insect cage, different from the first opening in the first insect cage, configured to drain the cleaning liquid and debris remaining from farming insects in the first insect cage, wherein the top wall comprises a concave surface, seen from the interior side of the first insect cage; and
   a gas drying apparatus comprising:
      a ventilator for generating a gas flow;
      a third pipe coupled to a third opening of the insect cage for transporting the gas flow inside the first insect cage, a fourth opening of the first insect cage for releasing the gas out of the first insect cage, and
      a heater for heating the generated gas flow.

2. The insect breeding device according to claim 1, wherein the second opening of the first insect cage is located in a side wall of the side walls of the first insect cage, in a portion of said side wall where the bottom floor and the side wall provided with the second opening intersect, such that the second opening is located at the lowest point of the first insect cage relative to the horizontal when the side wall of the first insect cage is directed vertically.

3. The insect breeding device according to claim 1, wherein the second opening of the first insect cage is located in the bottom floor, such that the second opening is located at the lowest point of the first insect cage relative to the horizontal when the side walls of the first insect cage are directed vertically.

4. The insect breeding device according to claim 1, further comprising
   a liquid clearance device coupled to the second pipe and the bin, and comprising:
      a filter configured to separate the cleaning liquid from the debris and to deliver the cleaning liquid to the bin through a fifth pipe, wherein the filter comprises
      a sieve configured to separate the debris from the cleaning liquid, and
      a debris receptacle, configured to collect the debris separated by the sieve.

5. The insect breeding device according to claim 1, wherein the cleaning liquid further comprises water and at least one non-foaming detergent, wherein the cleaning liquid comprises between 0.5 percent and 10 percent of the non-foaming detergent by volume of the total cleaning liquid.

6. The insect breeding device according to claim 1, wherein
the nozzle is a fluid nozzle comprising one of a spiral liquid spray nozzle, a full-cone nozzle, a deflector plate nozzle, a solid jet nozzle, and a nozzle with a rotating head.

7. The insect breeding device according to claim 1, further comprising
a first valve, coupled to the first opening, configured to open or close the first opening, and
a second valve, coupled to the second opening, configured to open or close the second opening.

8. The insect breeding device according to claim 1, wherein the first insect cage comprises a substantially block shape comprising rounded corners in the inner surface of the first insect cage.

9. The insect breeding device according to claim 1, wherein the first insect cage is manufactured using rotation molding of a polymer blend.

10. The insect breeding device according to claim 1, wherein the first insect cage further comprises a tapered bottom floor surface at the interior of the first insect cage, the tapering directed such that the second opening is located at the lowest point of the first insect cage relative to the horizontal when the side walls of the first insect cage are directed vertically.

11. The insect breeding device according to claim 1, wherein the nozzle is further configured to have a spray angle between 240 degrees and 300 degrees for a solid nozzle, or between 90 degrees and 120 degrees for a spiral nozzle, and
a spray pattern arranged as a solid cone or solid jets from a sphere.

12. The insect breeding device according to claim 1, wherein the nozzle is arranged to be positioned centrally in an inner volume of the first insect cage.

13. The insect breeding device according to claim 1, wherein the first insect cage comprises a further nozzle, the nozzles being positioned off-center, in the inner volume of the first insect cage.

14. An insect breeding device comprising:
at least one insect cage, the insect cage comprising a bottom floor, side walls and a top wall;
a bin for holding a cleaning liquid;
a first pipe connected to the bin for receiving the cleaning liquid, wherein the first pipe enters a first insect cage from the at least one insect cage through a first opening in the first insect cage;
a nozzle, coupled to the first pipe, positioned inside the first insect cage configured to deliver the cleaning liquid to the interior of the first insect cage;
a second pipe, coupled to a second opening in the first insect cage, different from the first opening in the first insect cage, configured to drain the cleaning liquid and debris remaining from farming insects in the first insect cage, wherein the top wall comprises a concave surface, seen from the interior side of the first insect cage, and further comprising
a first pump, positioned between the first opening and the bin, configured to deliver cleaning liquid to the interior of the first insect cage with a predetermined flow rate and a predetermined liquid pressure,
wherein the liquid pressure is in the range between 1.5 and 6 bar, and
wherein the volume of cleaning liquid delivered into the first cage is in the range between 10 liters and 500 liters per minute.

15. The insect breeding device according to claim 14, and further comprising
a second pump, positioned between the second opening and the bin, configured to drain the cleaning liquid and debris from the first insect cage to the bin.

16. The insect breeding device according to claim 15, further comprising
a third valve coupled to the third opening configured to open or close the third opening, and
a fourth valve coupled to the fourth opening configured to open or close the fourth opening.

17. The insect breeding device according to claim 16, further comprising
a controller connected to the first valve and the second valve and the first pump and second pump, wherein the controller is arranged to switch between a first state and a second state; wherein
in the first state the first and second valves are closed and the first and second pumps are switched off,
in the second state, the first valve is open and the second valve is open, the first pump is switched on and the second pump is switched on, wherein the controller is further arranged to maintain the second state for a period between 2 minutes and 180 minutes.

18. The insect breeding device according to claim 17, further comprising
a heater arranged between the bin and the first pump connected to the controller, wherein the heater is further arranged to deliver the cleaning liquid to the first pump at a temperature in the range of 20° C.-85° C.

19. An insect breeding device comprising:
at least one insect cage, the insect cage having a bottom floor, side walls and a top wall;
a bin for holding a cleaning liquid;
a first pipe connected to the bin for receiving the cleaning liquid, wherein the pipe is entering a first insect cage of the at least one insect cage through a first opening in the first insect cage;
a nozzle, coupled to the first pipe, positioned inside the first insect cage configured to deliver the cleaning liquid to the interior of the first insect cage; and
a second pipe, coupled to a second opening in the first insect cage, different from the first opening in the first insect cage, configured to drain the cleaning liquid and debris remaining from farming insects in the first insect cage from the first insect cage, wherein the top wall has a concave surface, seen from the interior side of the first insect cage,
wherein the cleaning liquid comprises a mixture of potassium, amine compounds, silicates, phosphates, non-ionogenic and amphoteric humidifiers and complexing agents.

\* \* \* \* \*